US007526500B2

(12) United States Patent
Bannai et al.

(10) Patent No.: US 7,526,500 B2
(45) Date of Patent: Apr. 28, 2009

(54) PERFUME INFORMATION PROCESSING DEVICE, PERFUME INFORMATION PROCESSING SYSTEM, AND PERFUME CONVERSION TABLE GENERATING METHOD

(75) Inventors: Yuichi Bannai, Koganei (JP); Keiichi Murai, Tokyo (JP); Kenichi Okada, Tokyo (JP); Shutaro Aiba, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 394 days.

(21) Appl. No.: 11/120,949

(22) Filed: May 4, 2005

(65) Prior Publication Data
US 2005/0278224 A1 Dec. 15, 2005

(30) Foreign Application Priority Data
May 12, 2004 (JP) ............................. 2004-141736

(51) Int. Cl.
*G06F 7/00* (2006.01)
*G01N 33/00* (2006.01)
*C11D 3/50* (2006.01)
(52) U.S. Cl. .................... 707/102; 422/83; 510/101
(58) Field of Classification Search .................. 422/50, 422/57, 83, 85, 98; 510/100, 101
See application file for complete search history.

(56) References Cited

U.S. PATENT DOCUMENTS

| | | | | |
|---|---|---|---|---|
| 5,295,064 A | * | 3/1994 | Malec et al. | 705/1 |
| 6,360,584 B1 | * | 3/2002 | Okubo et al. | 73/23.34 |
| 6,439,026 B2 | * | 8/2002 | Nakano et al. | 73/23.34 |
| 6,507,802 B1 | * | 1/2003 | Payton et al. | 702/150 |
| 2001/0008611 A1 | | 7/2001 | Budman | 422/4 |
| 2002/0059217 A1 | | 5/2002 | Oya et al. | 707/4 |

(Continued)

FOREIGN PATENT DOCUMENTS

CN 1322144 11/2001

(Continued)

OTHER PUBLICATIONS

"Research and Study Meetings on Five-senses Information Communication Techniques," Ministry of Internal Affairs and Communications of Japan, Nov. 2000.

(Continued)

*Primary Examiner*—Christian P. Chace
*Assistant Examiner*—Tarek Chbouki
(74) *Attorney, Agent, or Firm*—Fitzpatrick, Cella, Harper & Scinto

(57) ABSTRACT

In a perfume information processing system, a WEB server that provides contents containing perfume information, a perfume inquiry server that generates a perfume conversion table, and multiple clients that each includes a perfume emitting device are connected to a network. Each client sends information showing a perfume that should be emitted and information showing each stored perfume of its corresponding perfume emitting device to the perfume inquiry server and retrieves a perfume conversion table for converting the perfume that should be emitted into information showing a stored perfume. The client converts the perfume information contained in the contents retrieved from the WEB server into perfume information by referring to the perfume conversion table and controls perfume emission by the corresponding perfume emitting device based on the perfume information, thereby performing perfume emission.

17 Claims, 26 Drawing Sheets

U.S. PATENT DOCUMENTS

| | | | |
|---|---|---|---|
| 2002/0194092 A1* | 12/2002 | Tolkowsky et al. | 705/27 |
| 2003/0109056 A1* | 6/2003 | Vossmeyer et al. | 436/169 |
| 2004/0101447 A1* | 5/2004 | Tajima et al. | 422/123 |
| 2005/0160789 A1* | 7/2005 | Freyer et al. | 73/23.34 |
| 2007/0020153 A1* | 1/2007 | Hyacinthe | 422/124 |

FOREIGN PATENT DOCUMENTS

| | | |
|---|---|---|
| CN | 1322144 A | 11/2001 |
| EP | 1 329 228 | 7/2003 |
| EP | 1329228 | 7/2003 |
| EP | 1329228 A1 | 7/2003 |
| JP | 11-316769 | 11/1999 |
| JP | 2002-200157 | 7/2002 |
| JP | 2003-076874 | 3/2003 |
| JP | 2003-76874 A | 3/2003 |
| JP | 200376874 | 3/2003 |
| JP | 2003-162212 | 6/2003 |
| WO | 99/38102 | 7/1999 |

OTHER PUBLICATIONS

"Canon Technology Highlights," Canon Catalog No. CTH08 0103P21, issued by Canon Kabushiki Kaisha, 2003.

"For Realization of Broadcasting with Perfume Information," Technical Report of the Institute of Image Information and Television Engineers, vol. 27, No. 64, pp. 31 to 34, Nov. 12, 2003.

* cited by examiner

FIG. 17

| PERFUME WATER A | DIRECT DESIGNATION | 1 | 327982 |
|---|---|---|---|

FIG. 18

| PERFUME DATA NAME | (DIRECT/INDIRECT) DESIGNATION | THE NUMBER OF PERFUME id | PERFUME id (0) | ... | KEYWORDS (n) |
|---|---|---|---|---|---|

| PERFUME TYPE IDENTIFIER | THE NUMBER OF KEYWORDS | KEYWORDS (0) | ... |
|---|---|---|---|

FIG. 19

| SCENE 1: NATURE | INDIRECT DESIGNATION | 0 |
|---|---|---|

| EFFECT PERFUME | 5 | HILL | ... | BABBLING STREAM |
|---|---|---|---|---|

FIG. 28

```
CONTENTS DATA

<PERFUME>
        <NAME> SCENE 1: NATURE </NAME>
        <DESIGNATION METHOD> INDIRECT </DESIGNATION METHOD>
        <THE NUMBER OF KEYWORDS> 5 </THE NUMBER OF KEYWORDS>
                <KEYWORDS 0> HILL </KEYWORDS 0>
                   . . . . .
                <KEYWORDS n> HILL </KEYWORDS n>
        <EMITTING TIME> 4.5 </EMITTING TIME>
        <EMITTING STRENGTH> 128 </EMITTING STRENGTH>
</PERFUME>
```

FIG. 29

CONVERTED DATA

```
<PERFUME>
    <NAME> SCENE 1: NATURE </NAME>
    <PERFUME 1>
        <PERFUME id1> 89473 </PERFUME id1>
        <EMITTING AMOUNT> 0.9 </EMITTING AMOUNT>
    </PERFUME 1>
    <PERFUME 2>
        <PERFUME id1> 987655 </PERFUME id1>
        <EMITTING AMOUNT> 0.3 </EMITTING AMOUNT>
    </PERFUME 2>
        . . . . .
    <PERFUME n>
        <PERFUME id1> 78644 </PERFUME id1>
        <EMITTING AMOUNT> 0.15 </EMITTING AMOUNT>
    </PERFUME n>
    <EMITTING TIME> 4.5 </EMITTING TIME>
</PERFUME>
```

FIG. 30

```
CONTENTS DATA

<PERFUME>
        <NAME> SCENE 1: NATURE </NAME>
        <DESIGNATION METHOD> INDIRECT </DESIGNATION METHOD>
        <THE NUMBER OF KEYWORDS> 5 </THE NUMBER OF KEYWORDS>
                <KEYWORDS 0> HILL </KEYWORDS 0>
                     . . . . .
                <KEYWORDS n> HILL </KEYWORDS n>
        <EMITTING START TIME> 127+3/30 </EMITTING START TIME>
        <EMITTING TIME> 4.5 </EMITTING TIME>
        <EMITTING STRENGTH> 128 </EMITTING STRENGTH>
</PERFUME>
```

FIG. 31

```
CONVERTED DATA

<PERFUME>
        <NAME> SCENE 1: NATURE </NAME>
        <PERFUME 1>
                <PERFUME id1> 89473 </PERFUME id1>
                <EMITTING AMOUNT> 0.9 </EMITTING AMOUNT>
        </PERFUME 1>
        <PERFUME 2>
                <PERFUME id1> 987655 </PERFUME id1>
                <EMITTING AMOUNT> 0.3 </EMITTING AMOUNT>
        </PERFUME 2>
                        . . . . .
        <PERFUME n>
                <PERFUME id1> 78644 </PERFUME id1>
                <EMITTING AMOUNT> 0.15 </EMITTING AMOUNT>
        </PERFUME n>
        <EMITTING START TIME> 127+3/30 </EMITTING START TIME>
        <EMITTING TIME> 4.5 </EMITTING TIME>
</PERFUME>
```

PERFUME INFORMATION PROCESSING DEVICE, PERFUME INFORMATION PROCESSING SYSTEM, AND PERFUME CONVERSION TABLE GENERATING METHOD

BACKGROUND OF THE INVENTION

1. Field of the Invention

The present invention relates to a perfume information processing device, a perfume information processing system, and a perfume conversion table generating method for perfume emission.

2. Related Background Art

In conventional information processing, generally, only information depending on the sense of sight and the sense of hearing has been a processing target, although a demand for more natural communication is increasing and, for instance, "Research and Study Meetings on Five-senses Information Communication Techniques" have been held by the Ministry of Internal Affairs and Communications of Japan since November, 2000.

Among the five-senses information, smell-sense information contains unique information, such as sensuous information giving a sense of existence or the like, which cannot be fully expressed with other sensory information and is capable of increasing a sense of realism of information. Therefore, commercialization of perfume information processing is desired.

As a conventional technique of the perfume information processing, in JP 11-316769 A, a virtual travel system is proposed in which a smell at an actual-scene point is detected using a sensor, a detection value is sent, and the smell is reproduced on a reception side by mixing aromatics in accordance with the detection value. Also, in JP 2002-200157 A, a smell emitting device is proposed with which when a smell material cartridge suited for contents exists, a smell material is sent out from the cartridge and when such a suited smell material does not exist, a warning is issued.

Further, in Japanese Patent Application Laid-open No. 2003-076874, a perfume delivery system is proposed in which information about perfumes that can be emitted at a terminal is supplied to a server, a perfume is selected based on the information at the server, reproduction data for the selected perfume is sent to the terminal, and the perfume is emitted at the terminal through heating of a perfume sheet corresponding to the reproduction data. Still further, in Japanese Patent Application Laid-open No. 2003-162212, a perfume information providing system is proposed which includes a user interface for changing perfume information provided from an information provider in accordance with a user's preference.

In the conventional perfume information processing, however, a chemical substance for perfume emission is predetermined for each perfume and when the chemical substance does not exist, the perfume emission is difficult.

SUMMARY OF THE INVENTION

An object of the present invention is to provide a perfume information processing device and a perfume information processing system that are capable of emitting various perfumes using limited perfume resources.

Another object of the present invention is to provide a perfume information processing device and a perfume information processing system that are capable of emitting more appropriate perfumes using prepared perfume resources.

According to one aspect, the present invention which achieves these objectives relates to a perfume information processing device connected to a perfume emitting device that performs perfume emission by emitting a stored perfume, comprising: perfume emitting device information retrieval means for retrieving information showing each stored perfume from the perfume emitting device as perfume emitting device information; perfume conversion table generating means for generating a perfume conversion table for converting a perfume that should be emitted by the perfume emitting device into information showing a stored perfume of the perfume emitting device based on information showing the perfume that should be emitted and the perfume emitting device information; and perfume emitting device control means for converting the perfume that should be emitted by the perfume emitting device into the information showing the stored perfume of the perfume emitting device by referring to the perfume conversion table and controlling the perfume emission by the perfume emitting device based on the information showing the stored perfume.

According to another aspect, the present invention which achieves these objectives relates to a perfume conversion table generating method comprising: inputting information showing a perfume that should be emitted by a perfume emitting device and information showing each stored perfume of the perfume emitting device; judging whether a perfume directly associated with the information showing the perfume that should be emitted is contained among the stored perfumes by referring to correspondences between perfume information and the perfumes and, when a result of the judgment is positive, selecting the perfume; selecting a perfume having a highest point with respect to the information showing the perfume that should be emitted from among the stored perfumes by referring to a point of each perfume with respect to the perfume information; and generating a conversion table where the information showing the perfume that should be emitted and the selected perfume are associated with each other.

Other objectives and advantages besides those discussed above shall be apparent to those skilled in the art from the description of a preferred embodiment of the invention which follows. In the description, reference is made to accompanying drawings, which form a part thereof, and which illustrate an example of the invention. Such example, however, is not exhaustive of the various embodiments of the invention, and therefore reference is made to the claims which follow the description for determining the scope of the invention.

BRIEF DESCRIPTION OF THE DRAWINGS

FIG. 17 shows a state where concrete values have been inputted into parameters of the format of the material perfume;

FIG. 18 shows a format of a sensibility perfume;

FIG. 19 shows a state where concrete values have been inputted into parameters of the format of the sensibility perfume;

FIG. 28 shows an example where the perfume data format is written in XML;

FIG. 29 shows an example where the perfume conversion table is written in XML;

FIG. 30 shows another example where the perfume data format is written in XML;

FIG. 31 shows another example where the perfume conversion table is written in XML.

DESCRIPTION OF THE PREFERRED EMBODIMENTS

Hereinafter, preferred embodiments of the present invention will be described in detail with reference to the accompanying drawings.

First Embodiment (Perfume Information Processing System)

Figure 1:
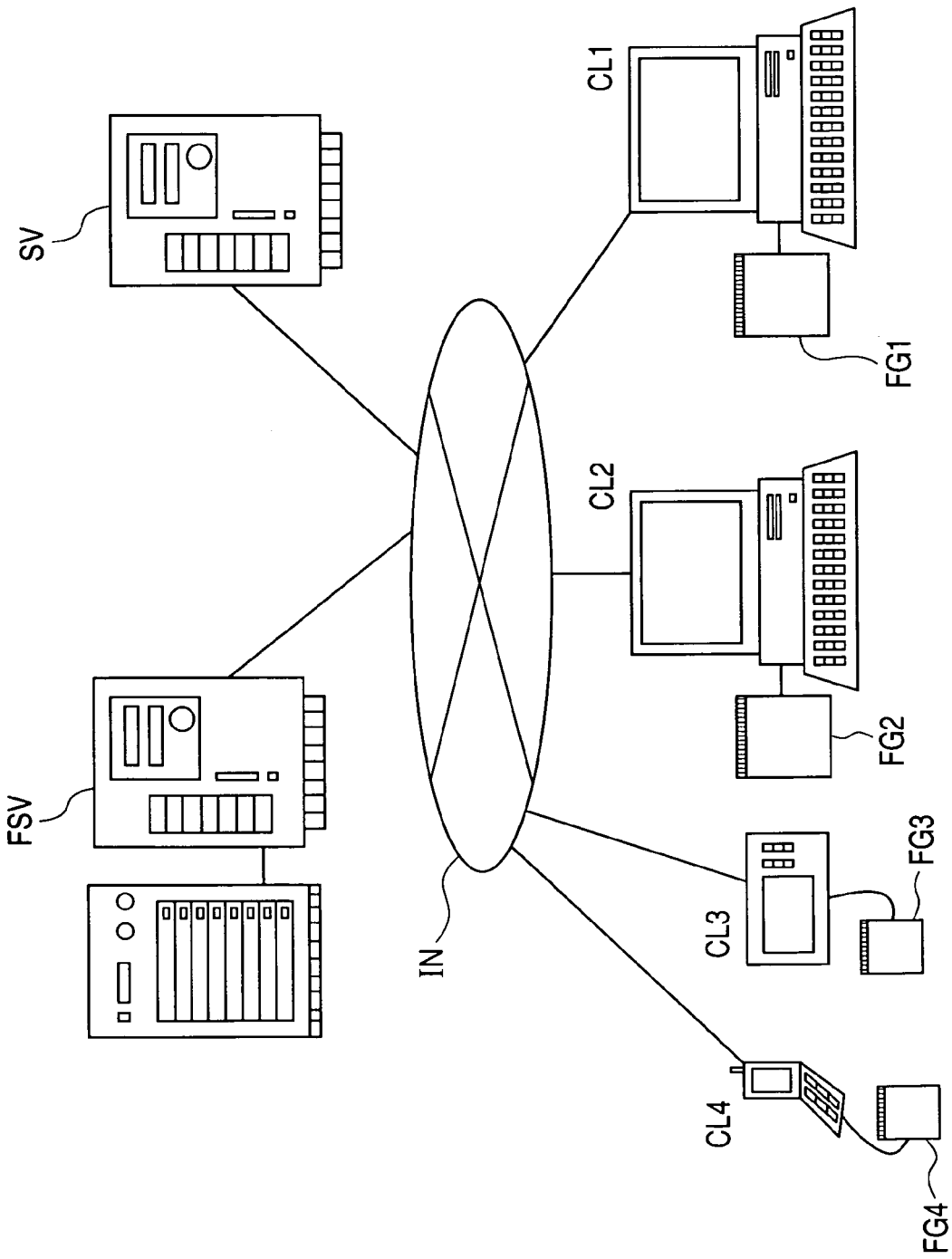
FIG. 1 is a block diagram showing a perfume information processing system in a first embodiment.

FIG. 1 is a block diagram showing a perfume information processing system according to a first embodiment.

In FIG. 1, in the perfume information processing system, a WEB server SV, a perfume inquiry server FSV, and clients CL1 to 4 are connected to a network IN such as the Internet.

The WEB server SV holds contents containing perfume information in a predetermined format, such as HTML, and the clients CL1 to 4 are capable of retrieving the contents from the WEB server SV through the network IN. As the clients, it is possible to adopt various equipment capable of connecting to the network IN. For instance, in the drawing, the clients CL1 and CL2 are each a personal computer, the client CL3 is a personal digital assistant (PDA), and the client CL4 is a mobile telephone.

The clients CL1 to 4 include perfume emitting devices FG1 to 4 respectively and are capable of emitting desired perfumes by controlling the perfume emitting devices FG1 to 4.

The clients CL1 to 4 emit perfumes based on the perfume information contained in the contents retrieved from the WEB server SV.

The clients CL1 to 4 each send the perfume information of the contents and information about corresponding one of the perfume emitting devices FG1 to 4 to the perfume inquiry server FSV and retrieve a perfume conversion table (to be described later) for control of the perfume emitting device and control of perfume designation (to be described later).

TABLE 1

| TYPE | | CHARACTERISTIC | APPLICATION | KEYWORD |
| --- | --- | --- | --- | --- |
| MATERIAL PERFUME | | PERFUME STEMMING FROM OBJECT | ONLINE SHOPPING | — |
| SENSIBILITY PERFUME | EFFECT PERFUME | PERFUME SUGGESTING SUBJECT | FOR SENSE OF REALISM IN MOVIE, VIDEO, OR THE LIKE | NOUN |
| | BACKGROUND PERFUME | PERFUME PROVIDING ATMOSPHERE (BGM) | | ADJECTIVE |
| | EMOTION PERFUME | PERFUME CORRESPONDING TO FEELING | ON-DEMAND AROMATIC | INTRANSITIVE VERB |

As shown in Table 1, in this embodiment, perfumes are classified into "material perfumes" and "sensibilities". The material perfumes are each a perfume stemming from an object, with an original perfume of the object being designated with one id number and one or more "replacement perfumes" that are capable of replacing the original perfume being each designated with an id number. The sensibilities are each a perfume where an atmosphere or the like expressed by the perfume is indirectly designated with a keyword and are classified into "effect perfumes", "background perfumes", and "emotion perfumes".

An example of the effect perfumes is a perfume, such as a burnt smell in a fire scene or a smell of gunpowder in a battle field scene, which suggests a subject in a movie. Also, the effect perfumes are each used to enhance a sense of realism and generally designated with a nominal keyword.

The background perfumes are each a perfume, such as a sweet perfume enhancing an atmosphere in a love scene of a movie, which provides an atmosphere like background music (BGM), and are generally designated with an adjectival keyword.

The emotion perfumes are each a perfume designated at the time of selection of an on-demand aromatic or the like, or in accordance with a user's feeling, such as a "desire to be relaxed", and are generally designated with an intransitive verbal keyword.

As distinct from the material perfumes, the sensibilities each have a possibility of being associated with multiple perfumes and are capable of increasing the number of selectable perfumes.

Figure 2:
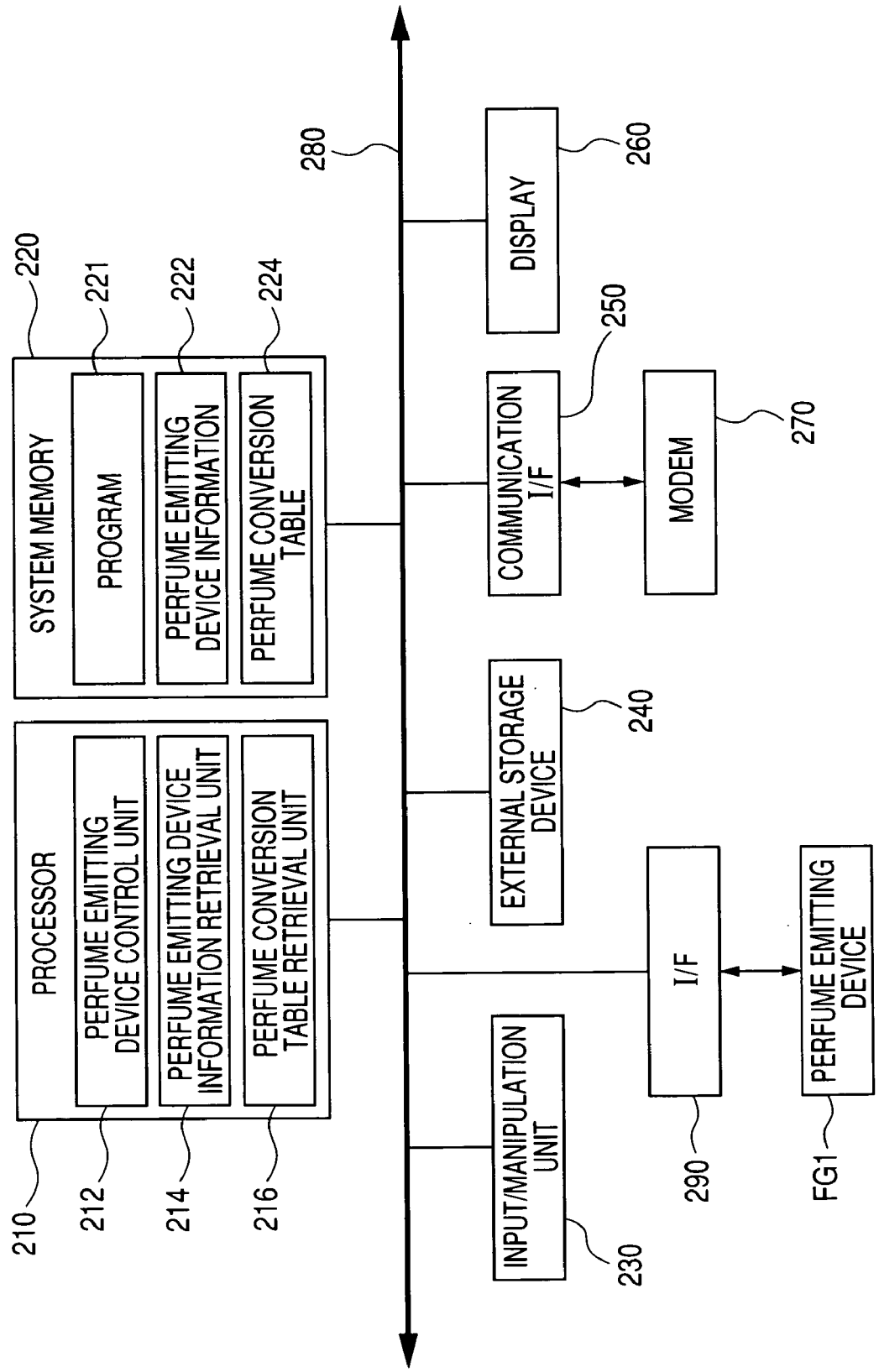
FIG. 2 is a block diagram showing an example of a construction of a perfume information processing device.

As a representative of the clients, the client CL1 will be described. FIG. 2 is a block diagram showing a hardware construction of a personal computer serving as the client CL1.

In FIG. 2, the personal computer serving as the client CL1 functions as the perfume information processing device and the perfume emitting device FG1 is connected to a system bus 280 through an interface 290 of the personal computer.

A processor 210 such as a CPU, a system memory 220, an input/manipulation unit 230, an external storage device 240, a communication interface 250, and a display 260 are also connected to the system bus 280.

The processor 210 functions as a perfume emitting device control unit 212 that controls the whole of the perfume information processing device. The processor 210 also functions as a perfume emitting device information retrieval unit 214 that retrieves information (perfume emitting device information 222) about perfumes that the perfume emitting device FG1 stores and a perfume conversion table retrieval unit 216 that retrieves a perfume conversion table 224 from the perfume inquiry server FSV. The perfume emitting device control unit 212 issues a perfume emitting instruction to the perfume emitting device FG1. It is possible to contain emitting strength and an emitting time in the perfume emitting instruction.

In the system memory 220, a program 221 for the perfume emitting device control unit 212 and other functions, the perfume emitting device information 222, the perfume conversion table 224, and the like are stored. The perfume conversion table 224 is retrieved from the perfume inquiry server FSV by the processor 210 that functions as the perfume conversion table retrieval unit 216.

A modem 270 is connected to the communication interface 250 and the perfume information processing device CL1 is connected to the network IN through the communication interface 250 and the modem 270.

The perfume emitting devices FG1 to FG4 are each constructed in the same manner. In FIGS. 3 to 8, the perfume emitting device FG1 is illustrated as a representative.

Figure 3:
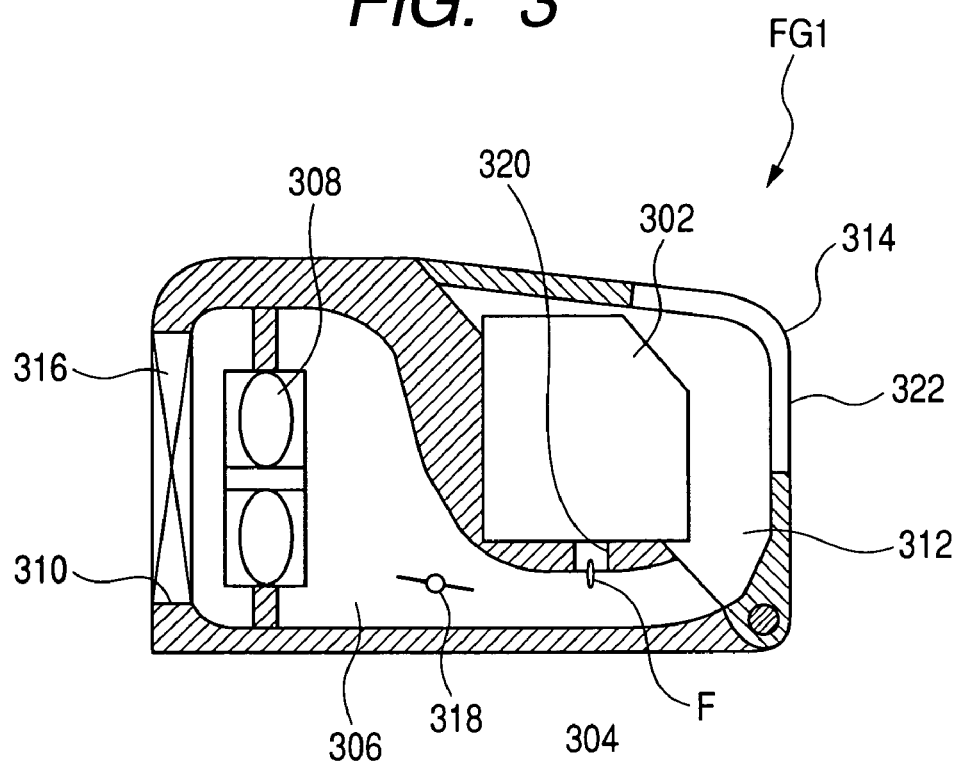
FIG. 3 is a vertical cross-sectional view of a perfume emitting device connected to the perfume information processing device.
Figure 4:
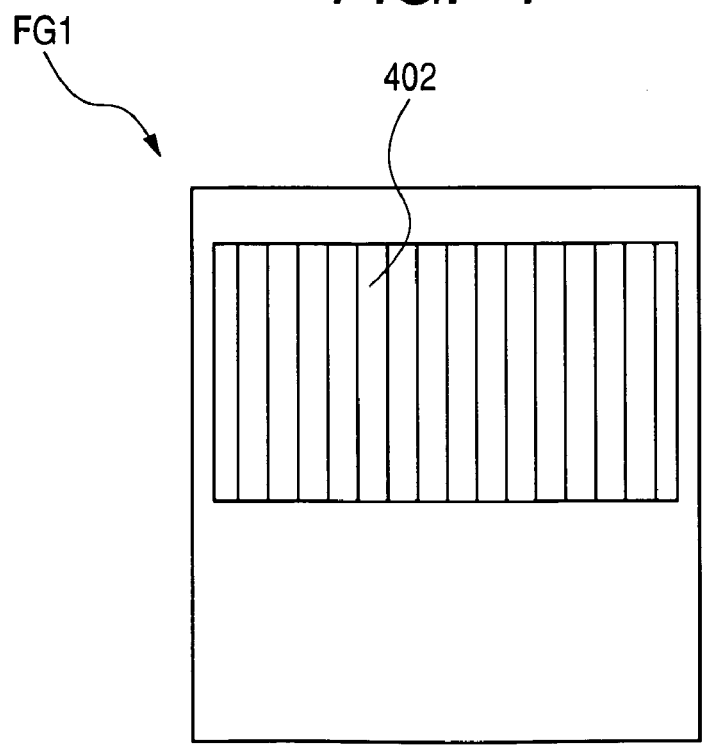
FIG. 4 is a right side view of the perfume information processing device.
Figure 5:
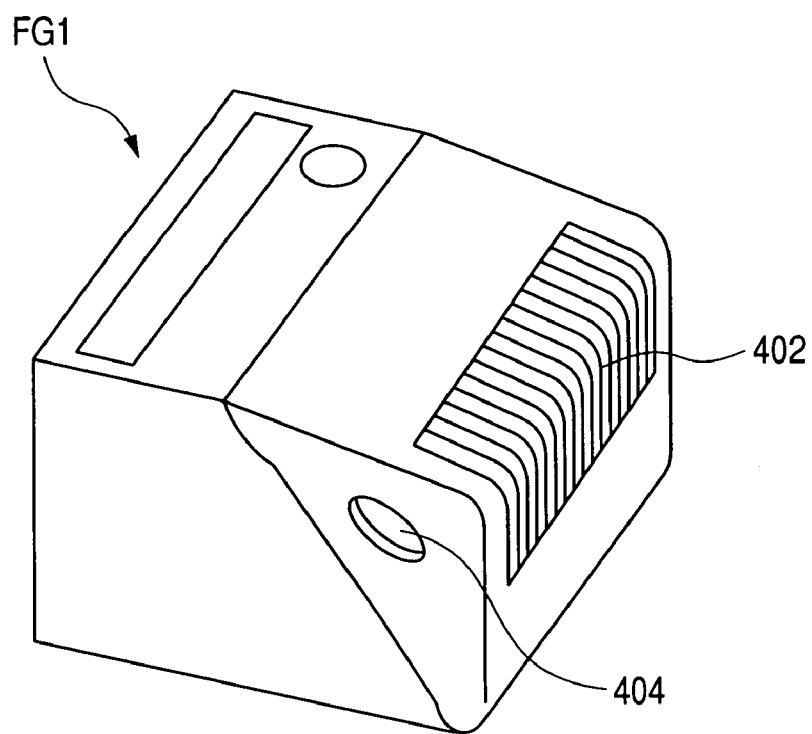
FIG. 5 is a perspective view where the perfume information processing device is viewed from the upper right.
Figure 6:
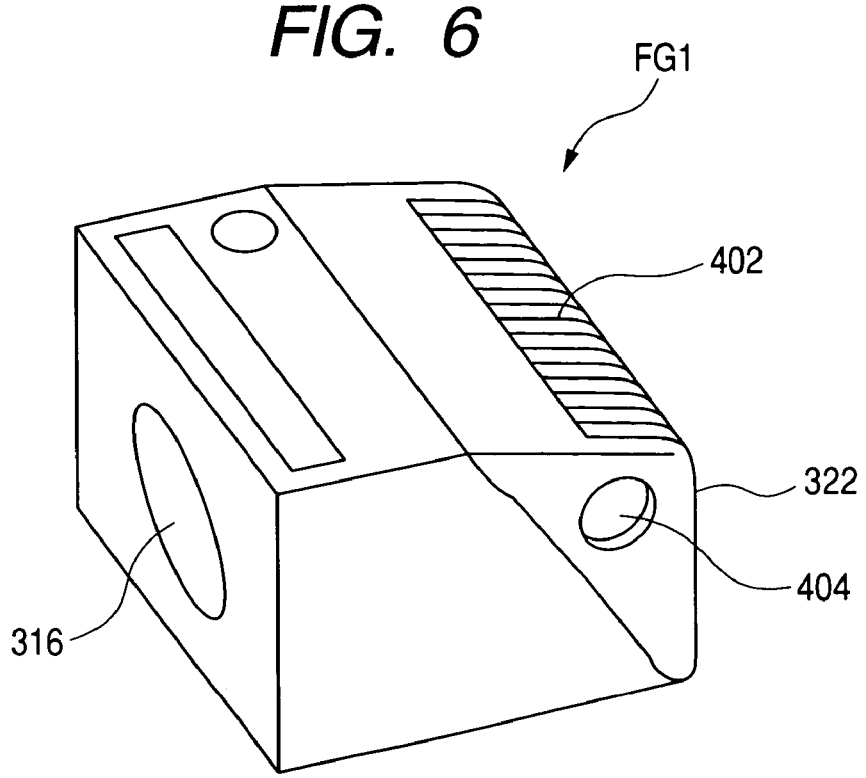
FIG. 6 is a perspective view where the perfume information processing device is viewed from the upper left.
Figure 7:
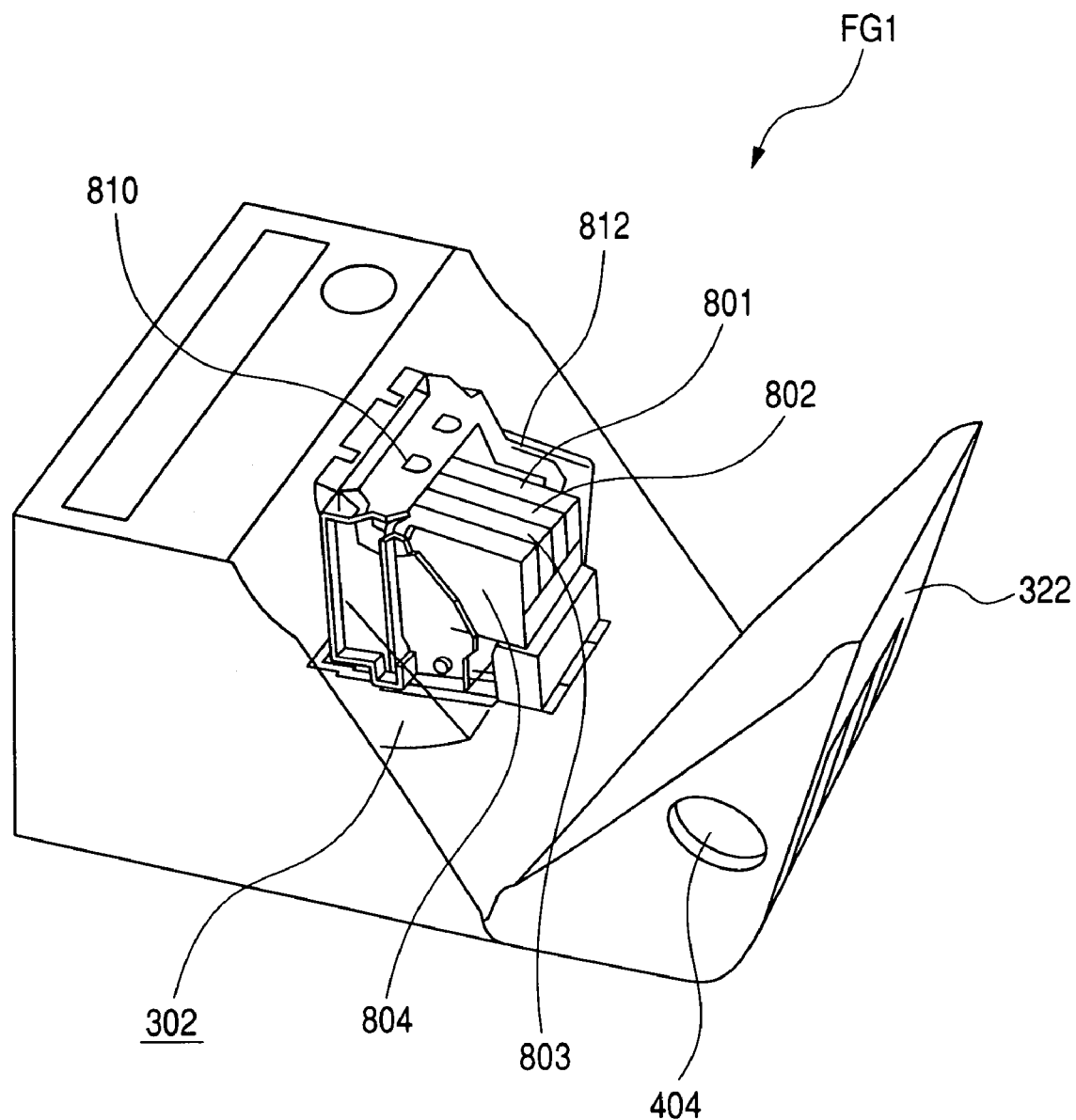
FIG. 7 is a perspective view showing a state where a cover of the perfume information processing device is opened.
Figure 8:
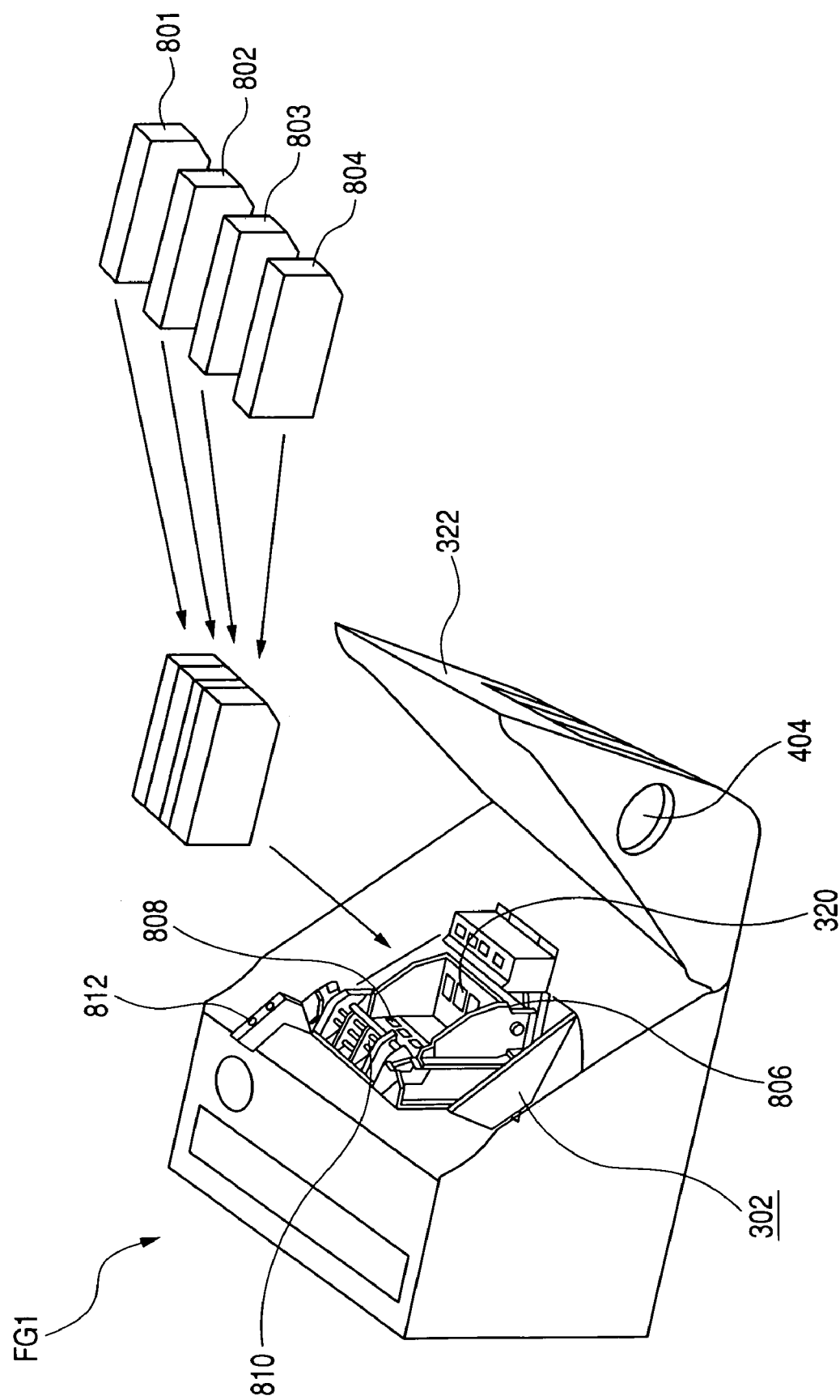
FIG. 8 is a perspective view showing attachment/detachment of perfume cassettes with respect to the perfume information processing device.

FIG. 3 is a vertical cross-sectional view of the perfume emitting device, FIG. 4 is a right side view of the perfume emitting device, FIG. 5 is a perspective view where the perfume emitting device is viewed from the upper right, FIG. 6 is a perspective view where the perfume emitting device is viewed from the upper left, FIG. 7 is a perspective view under a state where a cover of the perfume emitting device is opened, and FIG. 8 is a perspective view showing a state where the cover is opened and multiple perfume cassettes are mounted.

As shown in FIG. 3, the perfume emitting device FG1 includes an emitting portion 302 that emits a perfume F downwardly, with an air flow path 304 being provided below the emitting portion 302. A chamber portion 306 is formed on an upstream side of the air flow path 304 by increasing the cross-sectional area of the flow path and a fan 308 is arranged on an upstream side of the chamber portion 306.

In the perfume emitting device FG1, an air inflow opening 310 is formed on an upstream side of the fan 308 and the air is sucked through the air inflow opening 310 by the fan 308. The sucked air is sent and supplied to the chamber portion 306, is suppressed in pressure deviation, and is sent to the air flow path 304.

An emitting opening 320 opened toward the air flow path 304 is formed for the emitting portion 302 and the perfume F is emitted into the air flow path 304 through the emitting opening 320.

A flow path 312 extending upwardly is provided on a downstream side of the air flow path 304 and an end of the flow path 312 is set as an air exhaust opening 314. The air exhaust opening 314 is formed by multiple slits 402 (FIGS. 4 to 6) extending from the upper surface of the perfume emitting device FG1 to a side surface thereof.

A filter 316 is provided for the air inflow opening 310 which cleans and deodorizes the inflow air.

A valve 318 is provided between the chamber portion 306 and the air flow path 304 and is capable of adjusting the amount of the air flowing in the air flow path 304.

As shown in FIGS. 7 and 8, a holder portion 806 is provided for the emitting portion 302 which holds multiple perfume cassettes 801, 802, 803, and 804 filled with perfumes, and energizes a heater (not shown) that heats a nozzle (not shown) in each of the perfume cassettes 801 to 804 at appropriate times.

In each of the perfume cassettes 801 to 804, a bubble is generated in the perfume through the heating of the nozzle by the heater and a perfume droplet is separated and expelled from the nozzle by the action of the bubble. This is an application of the "MicroFine Droplet Technology" commercialized by the applicant of the present invention in the field of bubble jet printer to perfume emission.

The "MicroFine Droplet Technology" is described in a catalog "Canon Technology Highlights" (No. CTH08 0103P21) issued by the applicant of the present invention, for instance.

An electrode 808 for energizing the heater of each of the perfume cassettes 801 to 804 is provided in the holder unit 302.

The upper end of the emitting opening 320 is opened in the holder unit 302 and the perfume F emitted from each of the perfume cassettes 801 to 804 is emitted from the upper end portion of the emitting opening 320 downwardly.

The holder unit 302 is provided with a cramp 810 that fixes and holds each of the perfume cassettes 801 to 804 through pressurization and a lever 812 for vertically moving the cramp 810 is provided so as to protrude from the cramp 810.

An L-letter-shaped cover 322 extending from the right surface to the upper surface in FIG. 3 is provided for the perfume emitting device FG1 and is pivotally supported at its lower end. It is possible to expose the holder portion 302 to the outside as shown in FIGS. 7 and 8 by rotating the cover 322 about the pivotally supporting point at the lower end. Under the exposed state, it is possible to attach/detach the perfume cassettes 801 to 804 to/from the holder portion 302.

A concave portion 404 is formed on a side surface of the cover 322 in which a finger is put at the time of opening/closing of the cover 322.

A concave portion (not shown) indicating the type of the perfume F or an identifier portion by means of a barcode or the like is provided for each of the perfume cassettes 801 to 804 and the perfume emitting device FG1 discriminates the type of the perfume F (perfume emitting device information 222) by identifying the identifier portion.

The perfume emitting device control unit 212 of the perfume information processing device CL1 retrieves the perfume emitting device information 222 about the perfume cassettes 801 to 804 mounted to the perfume emitting device FG1 from the perfume emitting device FG1.

Figure 9:
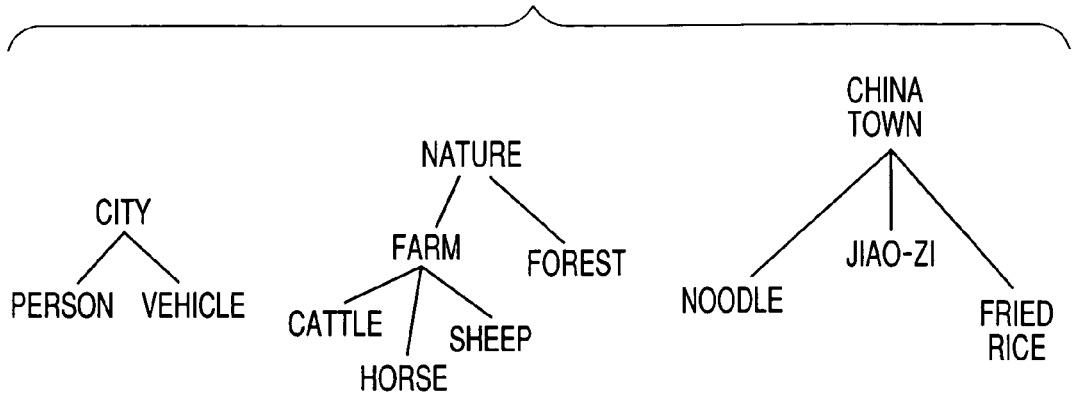
FIG. 9 shows layers of an effect perfume.

FIG. 9 shows a layer structure of the effect perfumes. For instance, a keyword "city" on the first layer is associated with keywords "person" and "vehicle" on the second layer giving lower concepts, and a keyword "nature" on the first layer is associated with keywords "farm" and "forest" on the second layer giving lower concepts. Also, the keyword "farm" on the second layer is associated with keywords "cattle", "horse", and "sheep" on the third layer giving lower concepts, and a keyword "China town" on the first layer is associated with keywords "Chinese noodle", "jiao-zi", and "fried rice" on the second layer giving lower concepts.

Those keywords are associated with perfumes in advance. For instance, as shown in Table 2, the keyword "Chinese noodle" is associated with a perfume id "1345", the keyword "jiao-zi" is associated with a perfume id "65314", and the keyword "fried rice" is associated with a perfume id "3816".

TABLE 2

|  | KEYWORD | | |
| --- | --- | --- | --- |
|  | CHINESE NOODLE | JIAO-ZI | FRIED RICE ... |
| PERFUME id | 1345 | 65314 | 3816 ... |

For instance, when perfume emission is requested using the keyword "China town", the perfume information processing device CL1 refers to the perfume emitting device information 222 retrieved from the perfume emitting device FG1. Following this, when a perfume corresponding to the keyword "China town" is stored, the perfume emission is performed using the perfume. On the other hand, when such a perfume corresponding to the keyword "China town" is not stored, the perfume emitting device information 222 searches for a perfume corresponding to the keyword "Chinese noodle", "jiao-zi", or "fried rice" on the second layer associated with the keyword "China town" on the first layer in FIG. 9. When it has been found as a result of the search that the perfume corresponding to the keyword on the second layer exists, perfume emission is performed using the perfume. On the other hand, when the perfume does not exist, the processing proceeds to the next layer within a predetermined search layer range. When the next layer does not exist or when no stored perfume exists in the search layer range, perfume emission is not performed.

As described above, the effect perfumes are defined in a layered manner, so even when a perfume corresponding to a desired effect perfume is not stored, there is a possibility that the desired effect perfume can be emitted using another perfume, which makes it possible to emit the desired effect perfume at various perfume emitting devices. That is, it is possible to increase the number of selectable perfumes. Note that a more complicated layer structure may occur, an example of which is a structure where multiple nominal keywords correspond to one nominal keyword on the next layer. Also, when multiple nominal keywords are set in advance, it becomes possible to further widen the selection range.

Table 3 shows relations between keywords for the background perfumes and perfumes.

TABLE 3

| | KEYWORD | | | | |
| --- | --- | --- | --- | --- | --- |
| PERFUME | REFRESHING | ROMANTIC | ELEGANT | UNPLEASANT | ... |
| LEMON | 95 | 60 | 50 | 10 | ... |
| GRAPEFRUIT | 85 | 50 | 60 | 10 | ... |
| ROSE | 70 | 80 | 90 | 15 | ... |
| JASMINE | 65 | 85 | 80 | 15 | ... |
| TOBACCO | 0 | 5 | 5 | 90 | ... |

In Table 3, for instance, the "lemon" perfume has points "95", "60", "50", and "10" with respect to the keywords "refreshing", "romantic", "elegant", and111 "unpleasant", respectively. The "grapefruit" perfume has points "85", "50", "60", and "10" with respect to the keywords "refreshing", "romantic", "elegant", and "unpleasant", respectively. The "rose" perfume has a point "70" "80", "90", and "15" with respect to the keywords "refreshing", "romantic", "elegant", and "unpleasant", respectively. The "jasmine" perfume has points "65", "85", "80", and "15" with respect to the keywords "refreshing", "romantic", "elegant", and "unpleasant", respectively. The "tobacco" perfume has points "0", "5", "5", and "90" with respect to the keywords "refreshing", "romantic", "elegant", and "unpleasant", respectively.

Hereinafter, for ease of explanation, it is assumed that only five perfumes that are the "lemon", "grapefruit", "rose", "jasmine", and "tobacco" perfumes exist in Table 3. When background perfume designation is made using the keyword "elegant", "rose" has the highest corresponding point in Table 3, so when the perfume emitting device CL1 stores the "rose" perfume, perfume emission is performed using the "rose" perfume. When the "rose" perfume does not exist, a perfume having the highest point as to the keyword "elegant" is selected from among the stored perfumes.

As described above, the background perfumes are defined with the points with respect to the keywords, so it is possible to select an optimum perfume from a wide selection range and it is also possible to widen the selection range through designation of multiple keywords.

Table 4 shows relations between keywords for the emotion perfumes and perfumes.

TABLE 4

| PERFUME | KEYWORD | | | |
|---|---|---|---|---|
| | DESIRE TO BE RELAXED | DESIRE TO BE EXCITED | DESIRE TO WAKEN UP | ... |
| LEMON | 50 | 60 | 80 | ... |
| MUSK | 10 | 90 | 60 | ... |
| LAVENDER | 90 | 5 | 50 | ... |
| PEPPERMINT | 40 | 75 | 90 | ... |

In Table 4, for instance, the "lemon" perfume has points "50", "60", and "80" with respect to the keywords "desire to be relaxed", "desire to be excited", and "desire to waken up", respectively. The "musk" perfume has points "10", "90", and "60" with respect to the keywords "desire to be relaxed", "desire to be excited", and "desire to waken up", respectively. The "lavender" perfume has points "90", "5", and "50" with respect to the keywords "desire to be relaxed", "desire to be excited", and "desire to waken up", respectively. The "peppermint" perfume has points "40", "75", and "90" with respect to the keywords "desire to be relaxed", "desire to be excited", and "desire to waken up", respectively.

Like in the case of the background perfumes, for emotion perfume emission, a perfume having the highest point with respect to a designated keyword is selected from among the stored perfumes.

Also, like in the case of the background perfumes, the emotion perfumes are defined with the points with respect to the keywords, so it is possible to select an optimum perfume from a wide selection range and it is also possible to widen the selection range through designation of multiple keywords.

Figure 15:
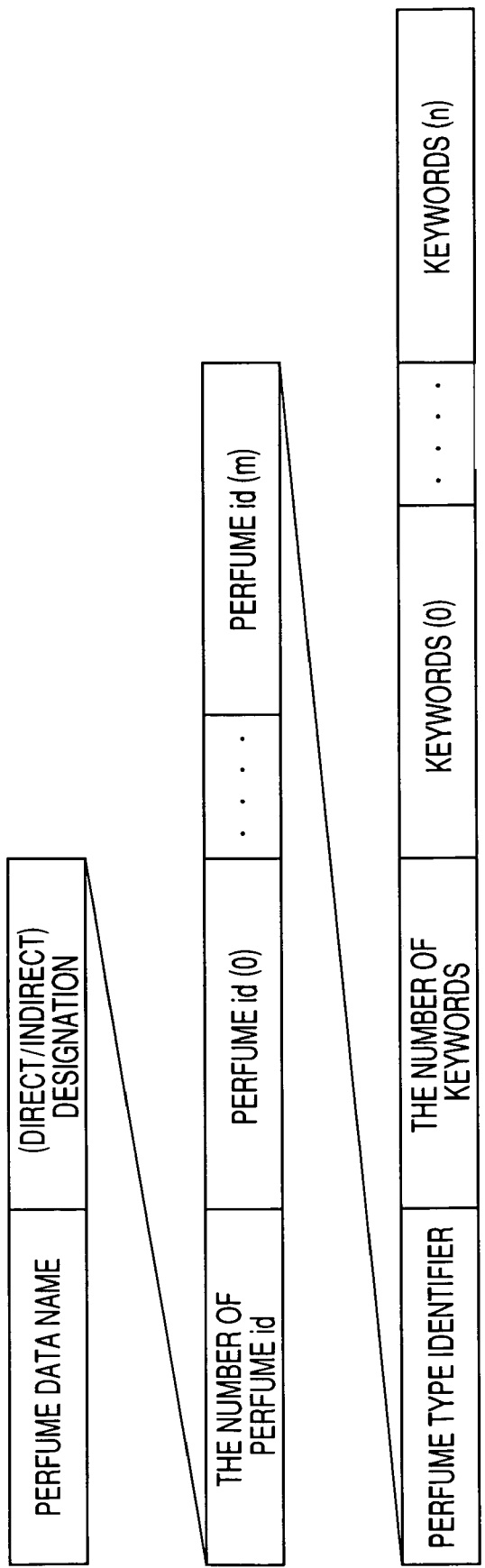
FIG. 15 shows a format of perfume data.

FIG. 15 shows a format of perfume information contained in contents that the client CL1 retrieves from the server SV.

In FIG. 15, the perfume information includes a "perfume data name" field, a "(direct/indirect) designation" field, a "the-number-of-perfume-ids" field, "perfume id" fields whose number is equal to a number designated in the "the-number-of-perfume-ids" field, a "perfume type identifier" field, a "the-number-of-keywords" field, and "keyword" fields whose number is equal to a number designated in the "the-number-of-keywords" field.

The "perfume data name" field gives a name or an ID number (corresponding to a file name) for identifying the perfume information and is set uniquely for each content so that it is possible to mutually identify the perfume information in each content.

The "(direct/indirect) designation" field gives a value indicating whether a perfume id is directly designated or a sensibility perfume is indirectly designated using a keyword, where it is also possible to make both of the direct designation and the indirect designation. When both of the direct designation and the indirect designation are made, the direct designation is given a higher priority. That is, when the perfume emitting apparatus stores a perfume having the directly designated perfume id, the indirectly designated sensibility perfume is not adopted.

The "the-number-of-perfume-ids" field gives a value indicating the number of perfume ids designated at the time of the perfume id direct designation. When the perfume id direct designation is not made, "0" is stored in the "the-number-of-perfume-ids" field.

The "perfume id" fields each give a perfume id designated at the time of the perfume id direct designation and perfume ids are designated whose number is equal to a number set in the "the-number-of-perfume-ids" field. The perfume ids are each given one of numbers of (0) to (the number of perfume ids). When the perfume id direct designation is not made, the "perfume id" fields are omitted.

The "perfume type identifier" field gives an identifier designating the type of the sensibility perfume, that is, one of the effect perfume, the background perfume, and the emotion perfume. When the perfume indirect designation is not made, the "perfume type identifier" field is omitted.

The "the-number-of-keywords" field gives a value indicating the number of keywords at the time of the sensibility perfume indirect designation. When the perfume indirect designation is not made, the fields following the "perfume type identifier" field are omitted.

The "keyword" fields each give a keyword designated at the time of the sensibility perfume indirect designation and keywords are designated whose number is equal to a number set in the "the-number-of-keywords" field. The keywords are each given one of numbers of (0) to (the number of keywords). When the sensibility perfume indirect designation is not made, the keyword fields are omitted.

Figure 16:
FIG. 16 shows a format of a material perfume.

As shown in FIGS. 16 and 17, perfume information about a material perfume is specified by one perfume. For instance, as to a material perfume having a perfume data name "perfume water A", "direct designation" is set in the "(direct/indirect) designation" field, "1" is set in the "the-number-of-perfume-ids" field, and a perfume id "327982" or the like is designated in the "perfume id (0)" field.

As shown in FIGS. 18 and 19, perfume information about a sensibility perfume is specified with one or multiple keywords. For instance, as to a sensibility perfume having a perfume data name "scene 1: nature", the (direct/indirect) designation is set at "indirect designation", the number of perfume ids is set at "0", and the perfume type identifier is set at "effect perfume". Also, for instance, the number of keywords is set at "5" and keywords like "hill" and "babbling stream" are designated whose number is equal to the set number of keywords.

When receiving a pair of the content perfume information and the perfume emitting device information described above, more specifically, a pair of the content perfume information and the identifier numbers of the perfume cassettes mounted to the emitting device from the perfume information processing device CL1, the perfume inquiry server FSV generates the perfume conversion table (Tables 5 and 6) for control of the perfume emitting devices FG1 to 4 and control of the perfume designation (to be described later) and sends it to the clients CL1 to CL4.

TABLE 5

| PERFUME DATA NAME | PERFUME id NUMBER |
|---|---|
| PERFUME WATER A | null |
| SCENE 1: NATURE | 89473 |
| SCENE 1: SMOKE | 489334 |
| SCENE 3: ANIMAL | null |

In Table 5, the perfume conversion table is a table for designating one perfume for a perfume id or a keyword and when the perfume emitting device does not store a given perfume, designation of "null (perfume emission will not be performed)" is made.

For instance, "null" is designated for the perfume data name "perfume water A", a perfume id "89473" is designated for the perfume data name "scene 1: nature", a perfume id "489334" is designated for the perfume data name "scene 1: smoke", and a perfume id "null" is designated for the perfume data name "scene 3: animal".

It is possible for the perfume information processing devices CL1 to CL4 to perform perfume emission immediately using the perfume emitting devices FG1 to FG4 based on the perfume conversion table.

TABLE 6

| PERFUME DATA NAME | PERFUME id NUMBER 1 | EMITTING AMOUNT | PERFUME id NUMBER 2 | EMITTING AMOUNT | ... | PERFUME id NUMBER n | EMITTING AMOUNT |
| --- | --- | --- | --- | --- | --- | --- | --- |
| PERFUME WATER A | 39839 | 1 | null | — | | null | — |
| SCENE 1: NATURE | 89473 | 0.9 | 987655 | 0.3 | | 78644 | 0.15 |
| SCENE 1: SMOKE | 489334 | 1 | null | — | | null | — |
| SCENE 3: ANIMAL | null | — | null | — | | null | — |
| ... | ... | ... | ... | ... | | ... | ... |

Table 6 shows another example of the perfume conversion table. In table 6, the perfume conversion table is capable of designating multiple perfumes and their emitting amounts with respect to a perfume id or a keyword, and when the perfume emitting device does not store given perfumes, designation of "null (perfume emission will not be performed)" is made.

For instance, as to the perfume data name "perfume water A", the emitting amount of a perfume having a perfume id "39839" is set at "1" (cc/sec) and emitting amounts corresponding to other perfume ids are each set at "null". Also, as to the perfume data name "scene 1: nature", the emitting amount of a perfume having a perfume id "89473" is set at "0.9" (cc/sec), the emitting amount of a perfume having a perfume id "987655" is set at "0.3" (cc/sec), and the emitting amount of a perfume having a perfume id "78644" is set at "0.15" (cc/sec). Further, as to the perfume data name "scene 1: smoke", the emitting amount of a perfume having a perfume id "489334" is set at "1" (cc/sec) and emitting amounts corresponding to other perfume ids are each set at "null". On the other hand, as to the perfume data name "scene 3: animal", the perfume id "null" is designated for every perfume.

As described above, it is also possible to express one perfume using multiple perfumes. This is applied to a case where a certain perfume is synthesized from other multiple perfumes and a case where multiple perfumes are associated with each nominal keyword in the case of the effect perfumes.

Also, in the case of the background perfumes and the emotion perfumes, processing is possible in which, for instance, several perfumes top-ranked as to a point with respect to a keyword, or several perfumes top-ranked as to a total value of points with respect to all keywords are selected.

Figure 20:
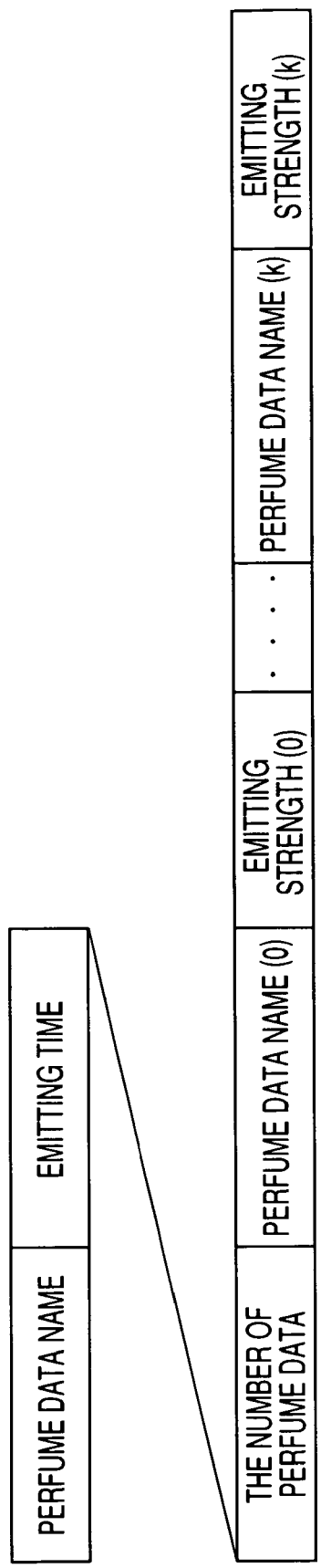
FIG. 20 shows another format of the perfume data.

Also, as shown in FIG. 20, perfume data composed of multiple pieces of perfume data may be defined. For instance, a "the-number-of-pieces-of perfume-data" field and multiple "perfume data" fields, whose number is equal to a value given in the "the-number-of-pieces-of-perfume-data" field, are provided. In addition, "emitting time" fields may be provided and emitting time may be set for the perfumes.

Further, in FIG. 20, an "emitting strength" field is provided so as to follow the "perfume data name" field for each perfume. The emitting strength is a ratio of the emitting amount of the perfume with respect to the maximum emitting amount (cc/sec) and is, for instance, defined with one of 256 levels expressed by 8-bit data. In the case of Table 6, the maximum emitting amount is 1 cc/sec and the emitting amounts of multiple perfumes are set for the perfume data "scene 1: nature".

The perfume information processing device CL1 or the like retrieved the perfume conversion table from the perfume inquiry server FSV is capable of emitting a perfume corresponding to the perfume information contained in the contents in the range of the perfumes that the perfume emitting device FG1 stores.

FIG. 28 is a drawing where the perfume data containing the emitting time and the emitting strength is expressed in an XML format, where the perfume data name being set at "scene 1: nature", the (direct/indirect) designation being set at "indirect", the number of keywords being set at "5", the keyword 0 being set at "hill", . . . , the keyword n being set at "babbling stream", the emitting time being set at "4.5", and the emitting strength being set at "128".

FIG. 29 shows an example where the perfume conversion table that converts the perfume data in FIG. 28 into a combination of multiple perfumes is expressed in an XML format. In FIG. 29, the perfume data name "scene 1: nature" is set, a perfume id "89473" and an emitting amount "0.9" are set for perfume 1, a perfume id "987655" and an emitting amount "0.3" are set for perfume 2, . . . , a perfume id "78644" and an emitting amount "0.15" are set for perfume n, and an emitting time "4.5" is set.

FIG. 30 is a drawing where the perfume data containing the emitting time, the emitting strength, and the emitting start time is expressed in an XML format, which is effective in the case of contents that are, for instance, stream data (time-series data of moving picture contents or the like). In the perfume data, like in FIG. 28, the perfume data name "scene 1: nature" is set, the (direct/indirect) designation is set at "indirect", the number of keywords is set at "5", the keyword 0 is set at "hill", . . . , the keyword n is set at "babbling stream", the emitting time is set at "4.5", and the emitting strength is set at "128". In addition, the emitting start time is set at "127+3/30", which indicates that the perfume emission is started at the 3/30-th frame after 127 seconds have passed from the start of the contents.

FIG. 31 shows an example where the perfume conversion table that converts the perfume data in FIG. 30 into a combination of multiple perfumes is expressed in an XML format. In the perfume conversion table, like in FIG. 29, the perfume data name "scene 1: nature" is set, a perfume id "89473" and an emitting amount "0.9" are set for perfume 1, a perfume id "987655" and an emitting amount "0.3" are set for perfume 2, . . . , a perfume id "78644" and an emitting amount "0.15" are set for perfume n, and an emitting time "4.5" is set. In addition, a value "127+3/30" is set as the emitting start time.

Figure 10:
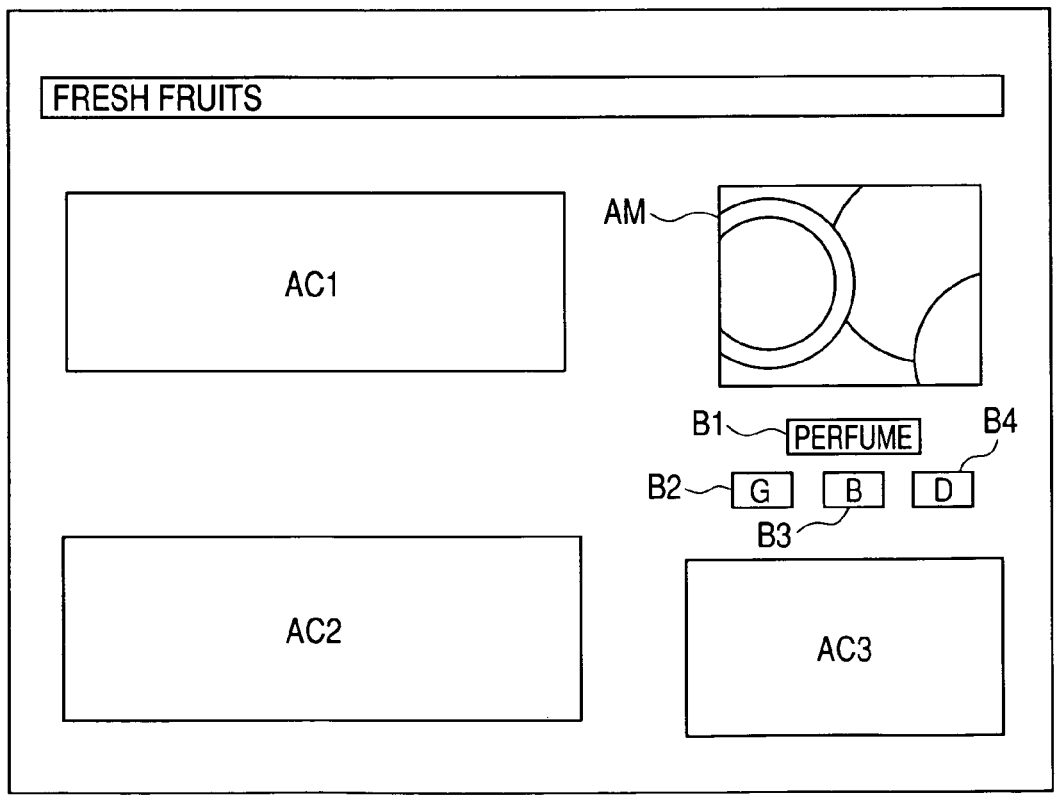
FIG. 10 shows a content display screen at the perfume information processing device.

FIG. 10 shows a state where contents containing character information areas AC1, AC2, and AC3 and an image information area AM are displayed on the display 260, with a "perfume" button B1 for perfume emission by the perfume emitting device FG1 being provided for a screen.

The "perfume" button B1 is arranged in proximity to the image information area AM and indicates that it is possible to emit a perfume corresponding to an image displayed in the image information area AM. For instance, an image of a lemon is displayed in the image information area AM and the perfume emitting device FG1 emits a perfume of the lemon in response to a click-on of the "perfume" bottom B1. Note that the arrangement of the "perfume" button B1 can be set in various manners in units of contents.

Also, a button B2 indicating that a perfume emitted from the perfume emitting device FG1 is "suitable", a button B3 indicating that the emitted perfume is "unsuitable", and a button B4 indicating that the emitted perfume is "unpreferable" are provided in proximity to the "perfume" button B1, thereby allowing a user to input his/her evaluation of the emitted perfume.

It is possible to apply the user's evaluation to amendments of the nominal keywords in the layer structure in FIG. 9, the relations between the effect perfumes and the perfume ids in Table 2, points with respect to the keywords as to the background perfumes in Table 3, and points with respect to the keywords as to the emotion perfumes in Table 4. That is, it is also possible to customize correspondences in FIG. 9 and Tables 2 to 4 in accordance with user's preference. Also, the user's evaluation may be reflected in content development afterward.

By emitting a perfume corresponding to the contents, a sense of realism is enhanced and it becomes possible for the user to feel an atmosphere or the like that cannot be sufficiently obtained only from an image.

Figure 11:
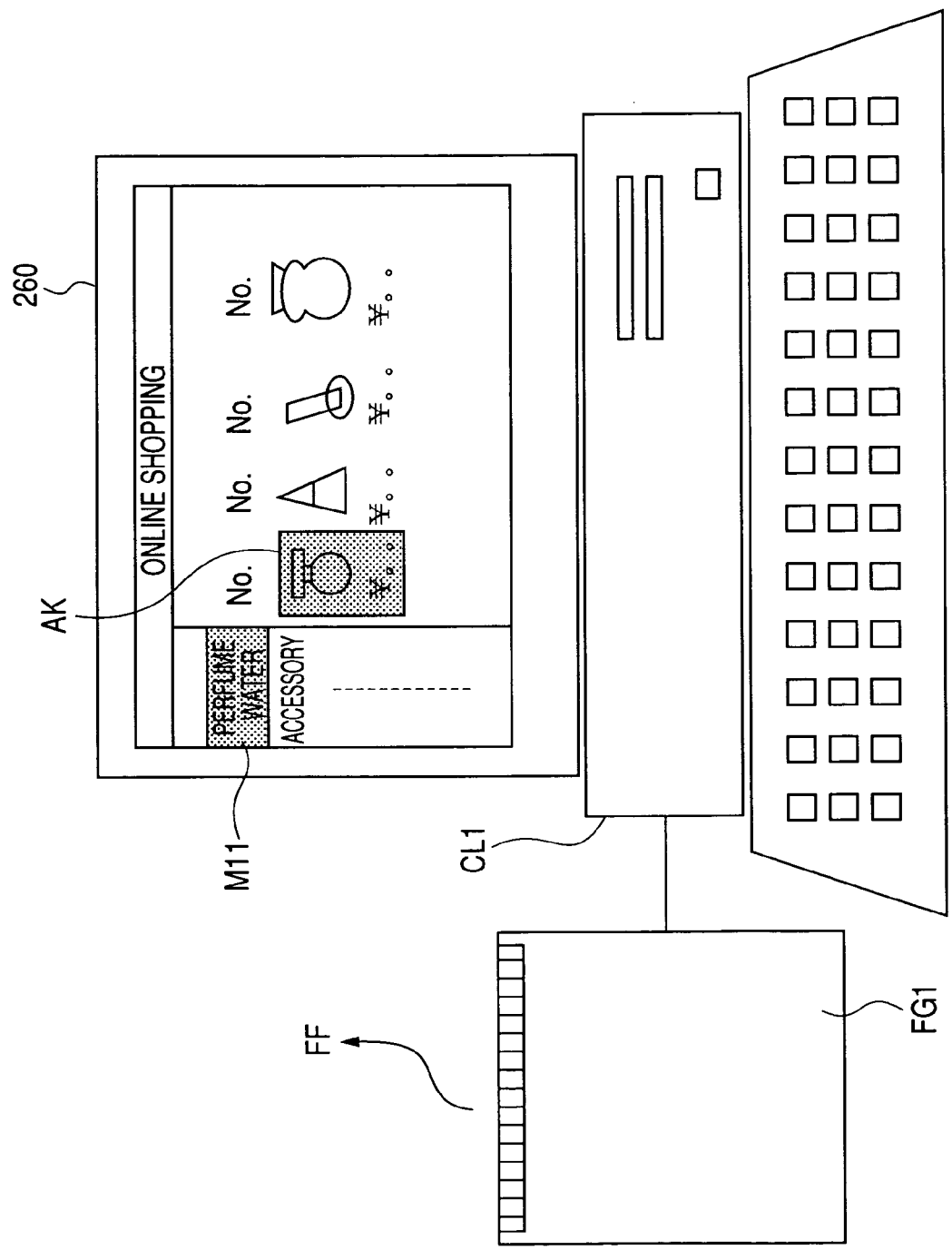
FIG. 11 shows another content display screen at the perfume information processing device.

FIG. 11 shows a state where the contents of online shopping are displayed on the display 260 of the perfume information processing device CL1, where multiple perfume water numbers and prices are displayed on the screen in response to a selection of a menu M11 for the perfume water.

For instance, when perfume water AK on the left end is selected, a perfume FF (material perfume) corresponding to the perfume water AK is emitted from the perfume emitting device FG1.

It should be noted here that in "For Realization of Broadcasting with Perfume Information" (Technical Report of the Institute of Image Information and Television Engineers, Vol. 27, No. 64, pp. 31 to 34, Nov. 12, 2003), Kenichi Okada and Syutaro Aiba, the inventors of the present invention, have confirmed psychological effects of a background perfume "rosemary" by classifying perfumes into the material perfumes aimed at precisely reproducing perfumes in the environment and the background perfumes (corresponding to the sensibilities in the present invention) aimed at psychological actions of sensing persons and by showing test subjects an image.

Figure 12:
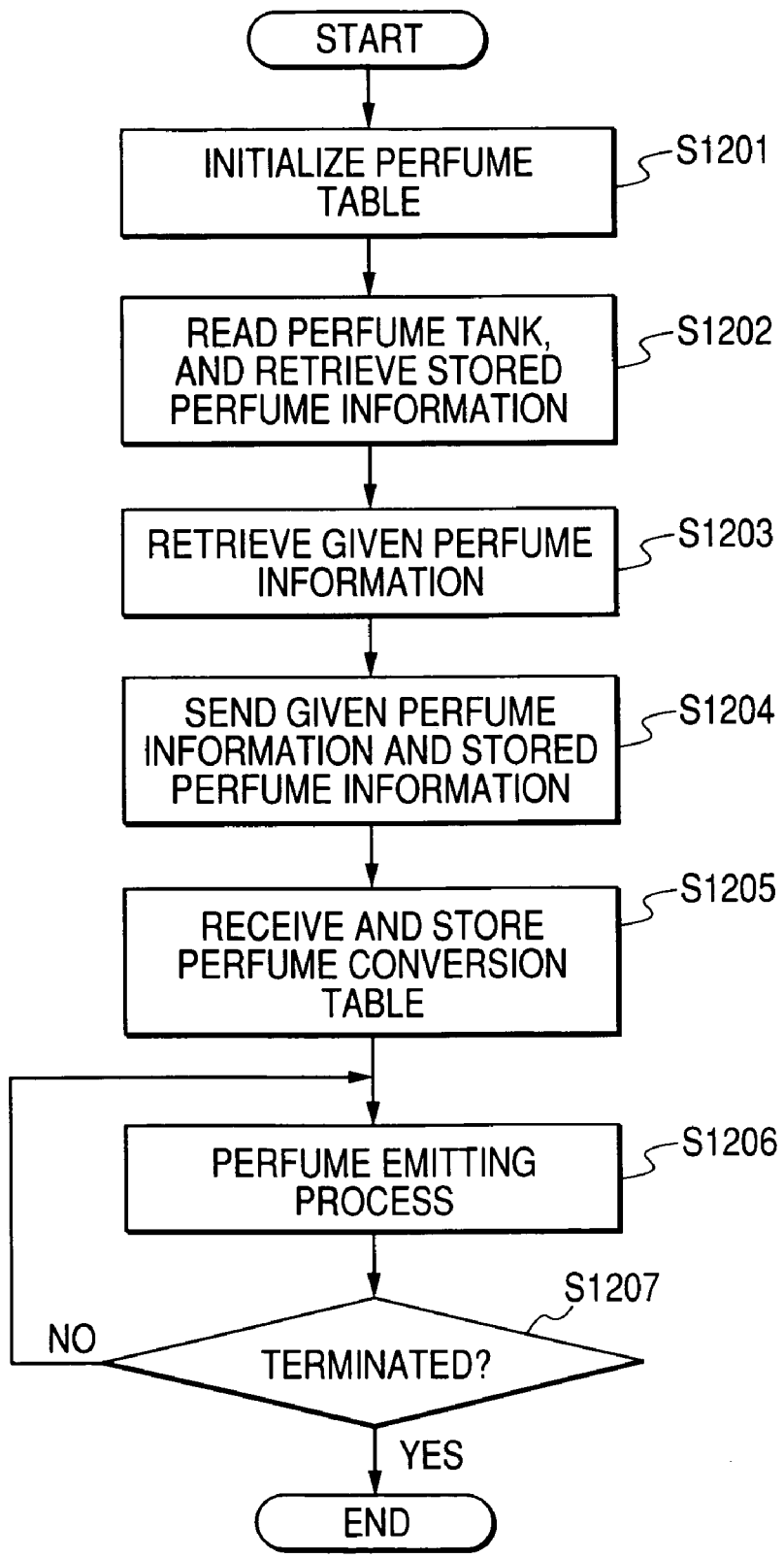
FIG. 12 is a flowchart showing a processing procedure of the perfume information processing device.
Figure 13:
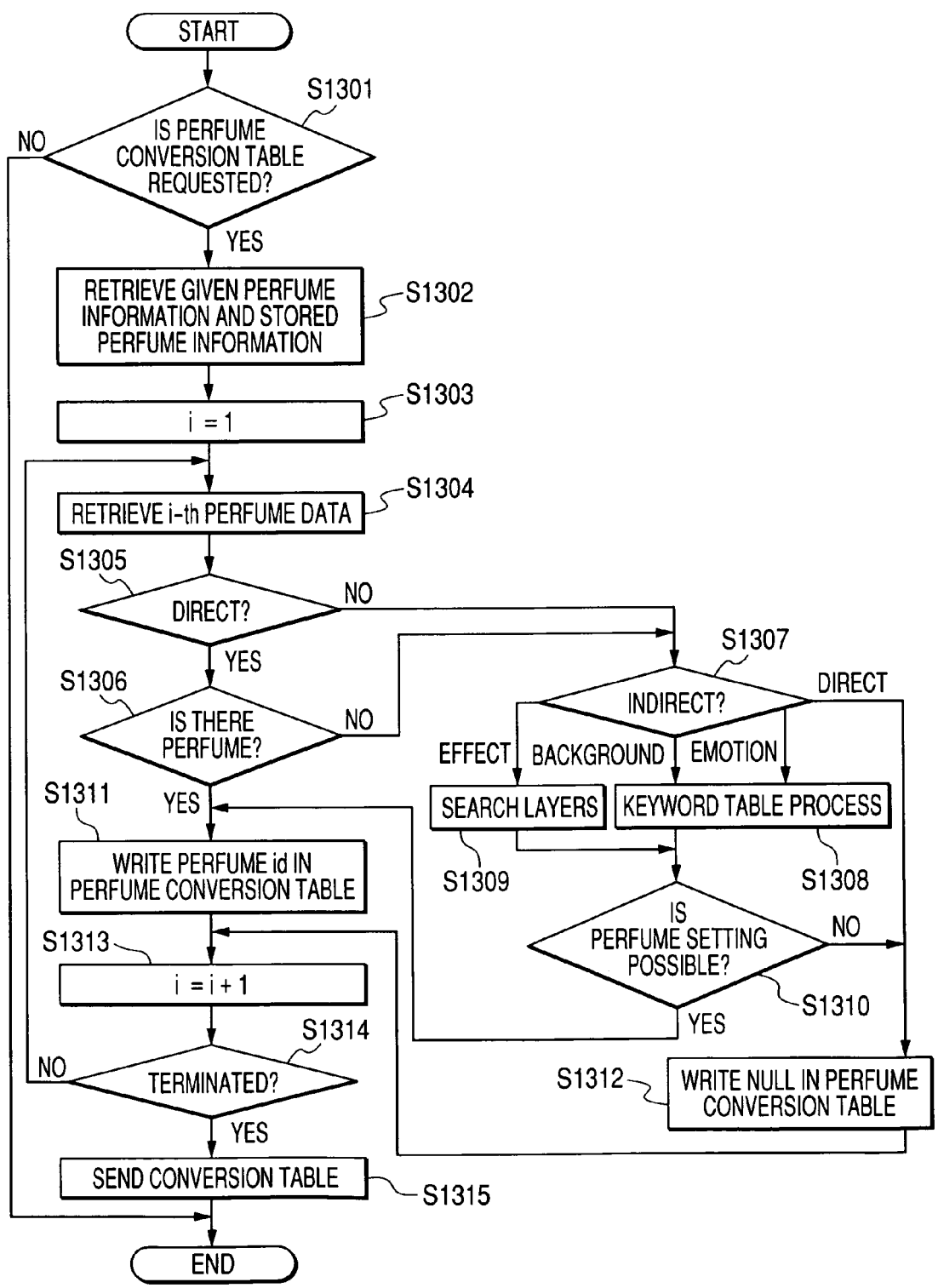
FIG. 13 is a flowchart showing a processing procedure of a perfume inquiry server.
Figure 14:
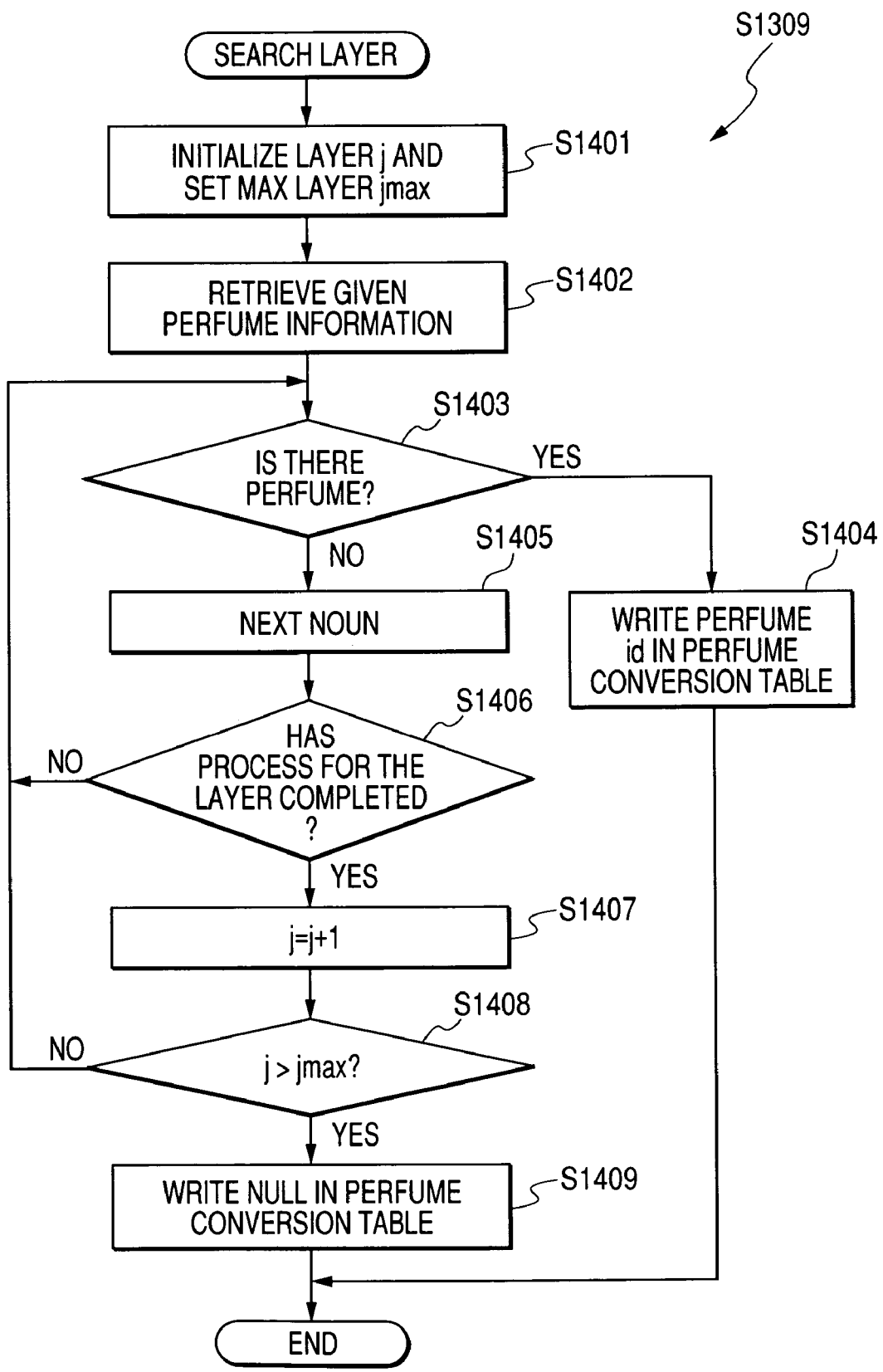
FIG. 14 is a flowchart showing a procedure of creation of an effect perfume conversion table.

FIG. 12 is a flowchart showing a processing procedure of the perfume information processing device CL1, FIG. 13 is a flowchart showing a processing procedure of the perfume inquiry server FSV, and FIG. 14 is a flowchart showing a processing procedure of layer search in FIG. 13.

In FIG. 12, the perfume information processing device CL1 retrieves the perfume information, retrieves the perfume conversion table, and then performs the perfume emission through respective steps described below.

In step S1201, prior to perfume emission based on new perfume information, first, the stored perfume conversion table 224 is initialized.

In step S1202 following step S1201, the perfume emitting device FG1 reads the identifier portions of the perfume cassettes 801 to 804 and the perfume information processing device CL1 retrieves this information (perfume types) as the perfume emitting device information 222.

Meanwhile, in step S1203, the perfume information processing device CL1 retrieves information (perfume information) about a perfume that is necessary in the contents or the like.

In step S1204 following step S1203, the perfume information processing device CL1 sends the perfume information and the perfume emitting device information to the perfume inquiry server FSV, thereby requesting a perfume conversion table. In response to this request, the perfume inquiry server FSV generates a perfume conversion table and sends it to the perfume information processing device CL1.

In step S1205 following step S1204, the perfume information processing device CL1 receives the perfume conversion table from the perfume inquiry server FSV and stores it in the system memory 220.

In step S1206 following step S1205, a perfume emitting process is repeated for the contents that are a processing target.

In step S1207, it is judged whether the perfume emitting process for the contents that are the processing target should be terminated. When a result of the judgment is negative, the processing returns to step S1206. On the other hand, when the judgment result is positive, the processing is terminated.

It should be noted here that it is also of course possible to execute each step in the processing shown in FIG. 12 after user's manipulation/input through, for instance, displaying of a message on the display 260.

In FIG. 13, the perfume inquiry server FSV retrieves the perfume information, retrieves the perfume emitting device information, and carries out a perfume conversion table generating/sending process through respective steps described below.

In step S1301, it is judged whether a perfume conversion table request has been received from the perfume information processing device CL1. Following this, when a result of the judgment is positive, the processing proceeds to operations in steps S1302 and later. On the other hand, when the judgment result is negative, the processing is terminated.

In step S1302, the perfume information and perfume emitting device information sent from the perfume information processing device CL1 are retrieved. Then, the processing proceeds to step S1303.

In step S1303, in order to process perfumes contained in the perfume information one at a time, a perfume counter i is initialized to "1".

In step S1304 following step S1303, the i-th perfume data (FIG. 15) is retrieved and each field is analyzed in the following processing.

In step S1305, it is judged whether direct designation is made by referring to the "(direct/indirect) designation" field. When the direct designation is made, the processing proceeds to step S1306. On the other hand, when the direct designation is not made, the processing proceeds to step S1307.

In step S1306, it is judged whether any of the perfumes having the perfume ids are contained in the perfume emitting device information by referring to the "the-number-of-perfume-ids" field and the "perfume id" fields. When a result of the judgment is positive, the processing proceeds to step S1311. On the other hand, when the judgment result is negative, the processing proceeds to step S1307. When multiple perfume ids are designated and multiple perfumes having the perfume ids are contained in the perfume emitting device information, an appropriate selection process is performed in which, for instance, a perfume id closer to the start (closer to the left in FIG. 15) is adopted.

In step S1307, it is judged whether indirect designation is made in the "(direct/indirect) designation" field. When indirect designation is made, the "perfume type identifier" field is referred to. In the case of a background perfume or an emotion perfume, the processing proceeds to step S1308. On the other hand, in the case of an effect perfume, the processing proceeds to step S1309. Also, when indirect designation is not made, the processing proceeds to step S1312.

In the case of a background perfume or an emotion perfume, in step S1308, a perfume having a higher point is selected from among perfumes contained in the perfume emitting device information by referring to the "the-number-of-keywords" field and the "keyword" fields and relations between the keywords and the perfumes (Tables 3 and 4).

On the other hand, in the case of an effect perfume, in step S1309, a perfume corresponding to the keyword is searched for from the perfume emitting device information by referring to the "the-number-of-keywords" field and the "keyword" fields. When such a perfume does not exist, a perfume corresponding to a keyword on a lower layer in the keyword layer structure (FIG. 9) is searched for from the perfume emitting device information. Step S1309 will be described in detail with reference to FIG. 14.

In step S1310, it is judged whether a perfume has been set through steps S1307 to S1309. When a result of the judgment is positive, the processing proceeds to step S1311. On the other hand, when the judgment result is negative, the processing proceeds to step S1312.

In step S1311, for the perfume data that is the processing target, a perfume id is written and the processing proceeds to step S1313.

In step S1312, for the perfume data that is the processing target, "null" is written and the processing proceeds to step S1313.

In step S1313, the perfume data counter i is incremented by "1" and the processing proceeds to step S1314.

In step S1314, it is judged whether every piece of perfume data has been processed. When any pieces of perfume data remain unprocessed, the processing returns to step S1304. On the other hand, when every piece of perfume data has been processed, the processing proceeds to step S1315.

In step S1315, a perfume conversion table is sent to the perfume information processing device CL1 and the processing is terminated.

In FIG. 14, the layer process (step S1309) in FIG. 13 is carried out through respective steps described below.

In step S1401, first, a layer counter j is initialized and the maximum depth value jmax is set for search target layers.

In step S1402, given perfume information is retrieved. Then, the processing proceeds to step S1403.

In step S1403, it is judged whether a perfume corresponding to a certain nominal keyword on the layer j is contained in the perfume emitting device information. When a result of the judgment is positive, the processing proceeds to step S1404. On the other hand, when the judgment result is negative, the processing proceeds to step S1405.

In step S1404, a perfume id contained in the perfume emitting device information is written in the perfume conversion table and the processing is terminated.

In step S1405, the next nominal keyword on the layer j is selected and the processing proceeds to step S1406.

In step S1406, it is judged whether every nominal keyword on the layer j has been processed. When any nominal keyword remains unprocessed, the processing returns to step S1403. On the other hand, when every nominal keyword has been processed, the processing proceeds to step S1407.

In step S1407, the layer counter j is incremented by "1". Then, the processing proceeds to step S1408.

In step S1408, it is judged whether the counter j has exceeded jmax. When a result of the judgment is negative, the processing returns to step S1403. On the other hand, when the judgment result is positive, the processing proceeds to step S1409.

In step S1409, no corresponding perfume exists, so "null" is written into the perfume conversion table for the perfume that is the processing target. Then, the processing is terminated.

Figure 21:
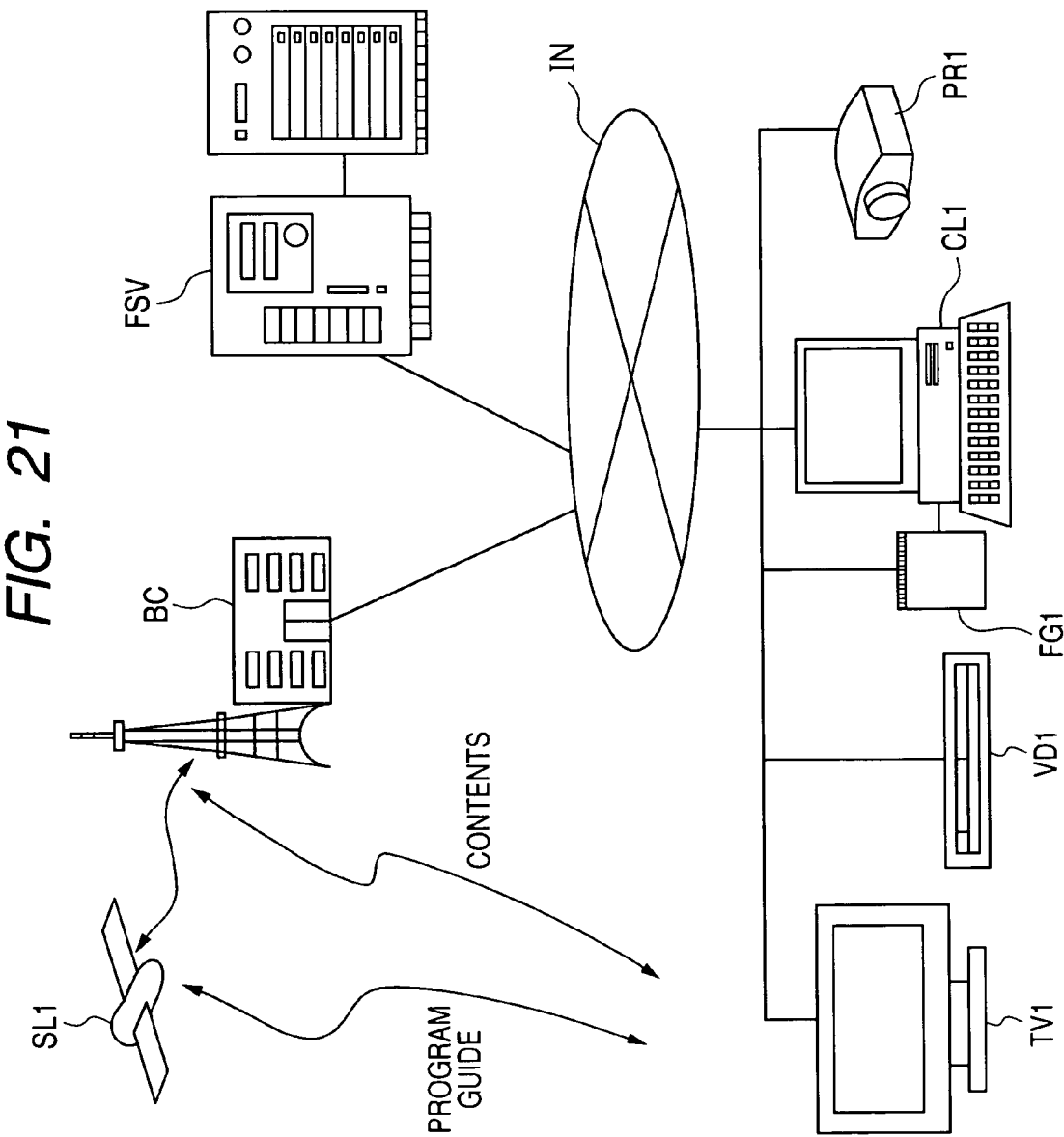
FIG. 21 is a block diagram showing an example where the perfume information processing system is applied to a broadcasting system.

FIG. 21 shows an example where the perfume information processing system is applied to a broadcasting system. In the drawing, each portion that is identical or equivalent to a portion in FIG. 1 is given the same reference symbol and the description thereof will be omitted.

In FIG. 21, the broadcasting system includes multiple clients (only one client CL1 is shown in the drawing) and a perfume inquiry server FSV connected to a network IN. To the client CL1, contents are provided from a broadcasting station BC and a program guide is provided from the broadcasting station BC or a broadcasting satellite SL.

Perfume information of each content is provided to the client CL1 by means of the program guide prior to program broadcasting or is provided to the client CL1 together with each content, a commercial, or the like.

The program guide is provided by a broadcasting radio wave from the broadcasting station BC or the broadcasting satellite SL or is provided through the network IN.

Devices for reproducing contents and recording contents as appropriate, such as a perfume emitting device FG1, a television set TV1, a video recording device VD1, and a projector PR1, are connected with various connection methods such as LAN or Bluetooth to the client CL1.

The client CL1 sends perfume information of contents and information about perfumes held in the perfume emitting device FG1 to the perfume inquiry server FSV and retrieves a perfume conversion table from the perfume inquiry server FSV.

Figure 22:
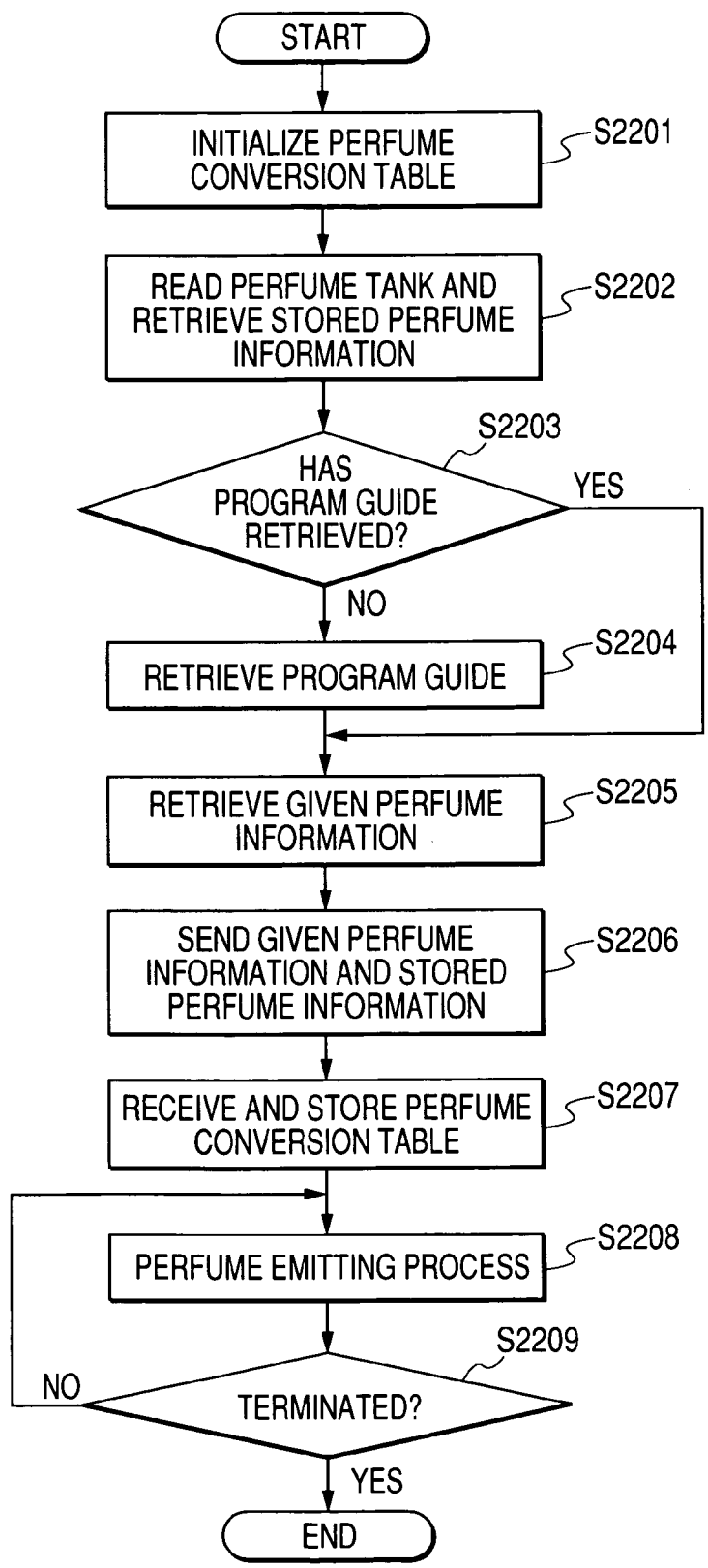
FIG. 22 is a flowchart showing processing of a client in the broadcasting system.

FIG. 22 is a flowchart showing processing of the client (perfume information processing device) CL1 in the broadcasting system.

In FIG. 22, the perfume information processing device CL1 retrieves the perfume information, retrieves the perfume conversion table, and then performs perfume emission through respective steps described below.

In step S2201, like in step S1201 shown in FIG. 12, the perfume conversion table 224 is initialized.

In step S2202, like in step S1202 shown in FIG. 12, perfume emitting device information of the perfume emitting device FG1 is retrieved.

In step S2203, it is judged whether information, such as a program guide, which contains perfume information of contents has been retrieved. When a result of the judgment is positive, the processing jumps to step S2205. On the other hand, when the judgment result is negative, the processing proceeds to step S2204.

In step S2204, information, such as a program guide, which contains perfume information of contents is retrieved. Then, the processing proceeds to step S2205.

In steps S2205 to S2209, like in steps S1203 to S1207 shown in FIG. 12, retrieval of the perfume information, sending of the perfume information and the perfume emitting device information, reception of the perfume conversion table, a perfume emitting process, and a termination judgment are performed. Processing of the perfume inquiry server FSV in generation and sending of the perfume conversion table is the same as that in FIGS. 1 and 13.

Through the processing described above, in the broadcasting system, it is possible to emit a perfume corresponding to contents. Note that in the processing described above, perfume information used in a television program is retrieved by means of a program guide, however in digital broadcasting, it is also possible to multiplex perfume information into a television program content itself and broadcast it. In this case, a construction is also possible in which, for instance, the client (perfume information processing device) CL1 receives every piece of perfume information, retrieves a perfume conversion table at a time of start of an ordinary television program or a commercial, and performs perfume emission in accordance with the progress of the television program.

It should be noted here that it is also of course possible to embed the function of the perfume information processing device CL1 in the television set TV1, the projector PR1, the video recording device VD1, or the like.

In addition, it is also of course possible to execute each step in the processing shown in FIG. 22 after user's manipulation/input through, for instance, displaying of a message on the display 260.

Figure 23:
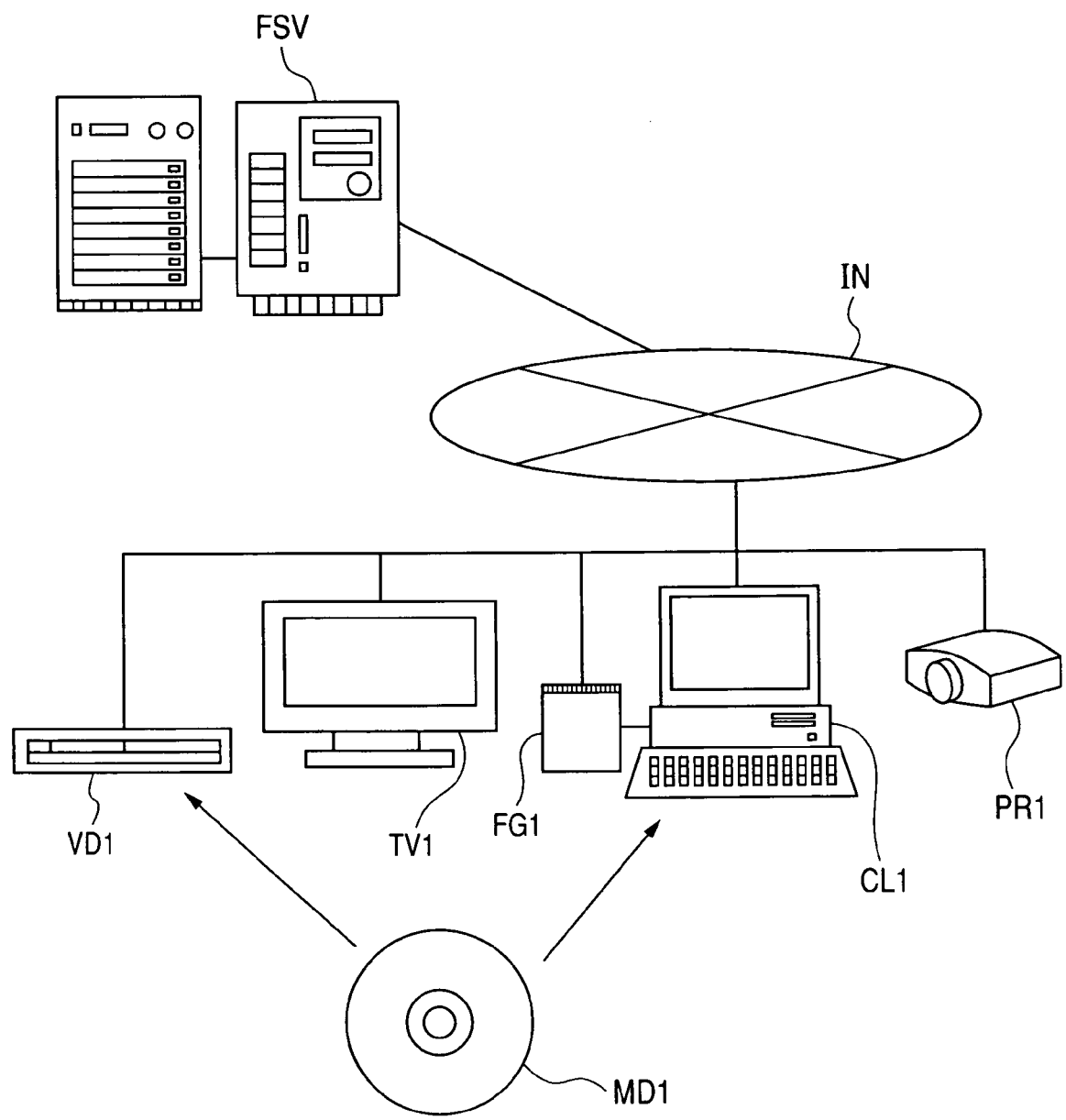
FIG. 23 is a block diagram showing an example where the perfume information processing system is applied to a media reproducing system.

FIG. 23 shows an example where the perfume information processing system is applied to a media reproducing system. In the drawing, each portion that is identical or equivalent to a portion in FIG. 21 is given the same reference symbol and the description thereof will be omitted.

In FIG. 23, the media reproducing system includes multiple clients (only one client CL1 is shown in the drawing) and a perfume inquiry server FSV connected to a network IN.

To the client CL1, devices for reproducing contents of a medium MD1 and recording the contents as appropriate, such as a perfume emitting device FG1, a television set TV1, a video recording device VD1, and a projector PR1, are connected with various connection methods.

The client CL1 sends perfume information of contents and information about perfumes held in the perfume emitting device FG1 to the perfume inquiry server FSV and retrieves a perfume conversion table from the perfume inquiry server FSV.

Figure 24:
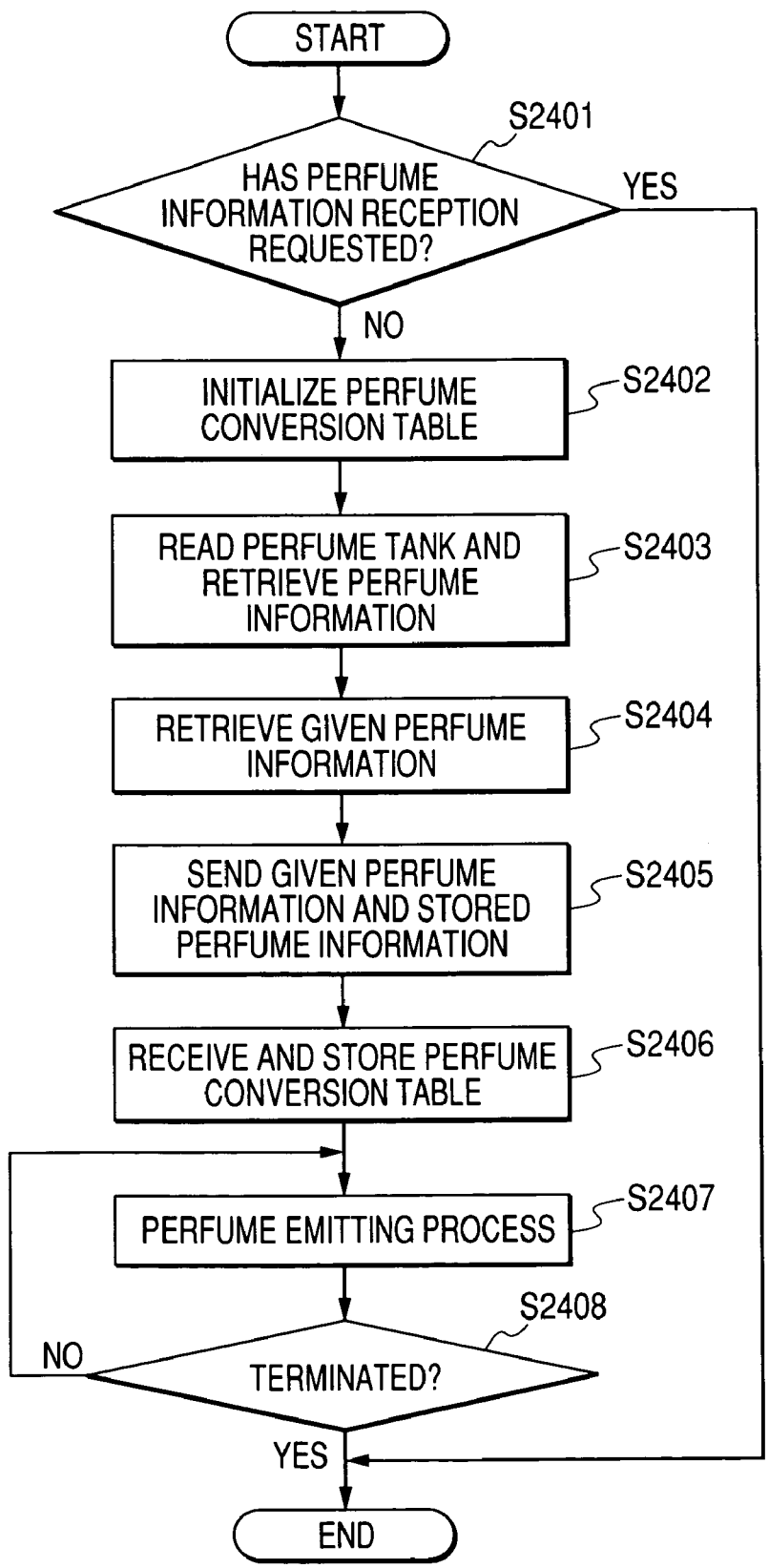
FIG. 24 is a flowchart showing processing of a client in the media reproducing system.

FIG. 24 is a flowchart showing processing of the client (perfume information processing device) CL1 in the media reproducing system.

In FIG. 24, the perfume information processing device CL1 retrieves perfume information, retrieves a perfume conversion table, and then performs perfume emission through respective steps described below.

In step S2401, when the contents of the media MD1 contains perfume information, a perfume information reception request is sent to the perfume information processing device CL1. It should be noted here that a notification to the effect that perfume information reception is required may be written in an instruction manual of the medium MD1 or information on a homepage or the like of a media publisher and a user may receive the perfume information based on the notification.

When the perfume information reception is required, the processing proceeds to step S2402. On the other hand, when the perfume information reception is not required, the processing is normally ended.

In steps S2402 to S2408, as in steps S1201 to S1207 in FIG. 12, perfume conversion table initialization, perfume emitting device information retrieval, perfume information retrieval, perfume information and perfume emitting device information sending, perfume conversion table reception, a perfume emitting process, and a termination judgment are carried out. Processing of the perfume inquiry server FSV in perfume conversion table generation and sending is the same as that in FIGS. 1 and 13.

Through the processing described above, in the media reproducing system, it is possible to emit perfume corresponding to contents.

It should be noted here that it is also of course possible to embed the function of the perfume information processing device CL1 in the television set TV1, the projector PR1, the video recording device VD1, or the like.

In addition, it is also of course possible to execute each step in the processing shown in FIG. 24 after user's manipulation/input through, for instance, displaying of a message on the display 260.

Also, a perfume cassette may be provided as an attachment for the medium MD1 and a user may set the cassette in the perfume emitting device FG1 and use it.

Figure 25:
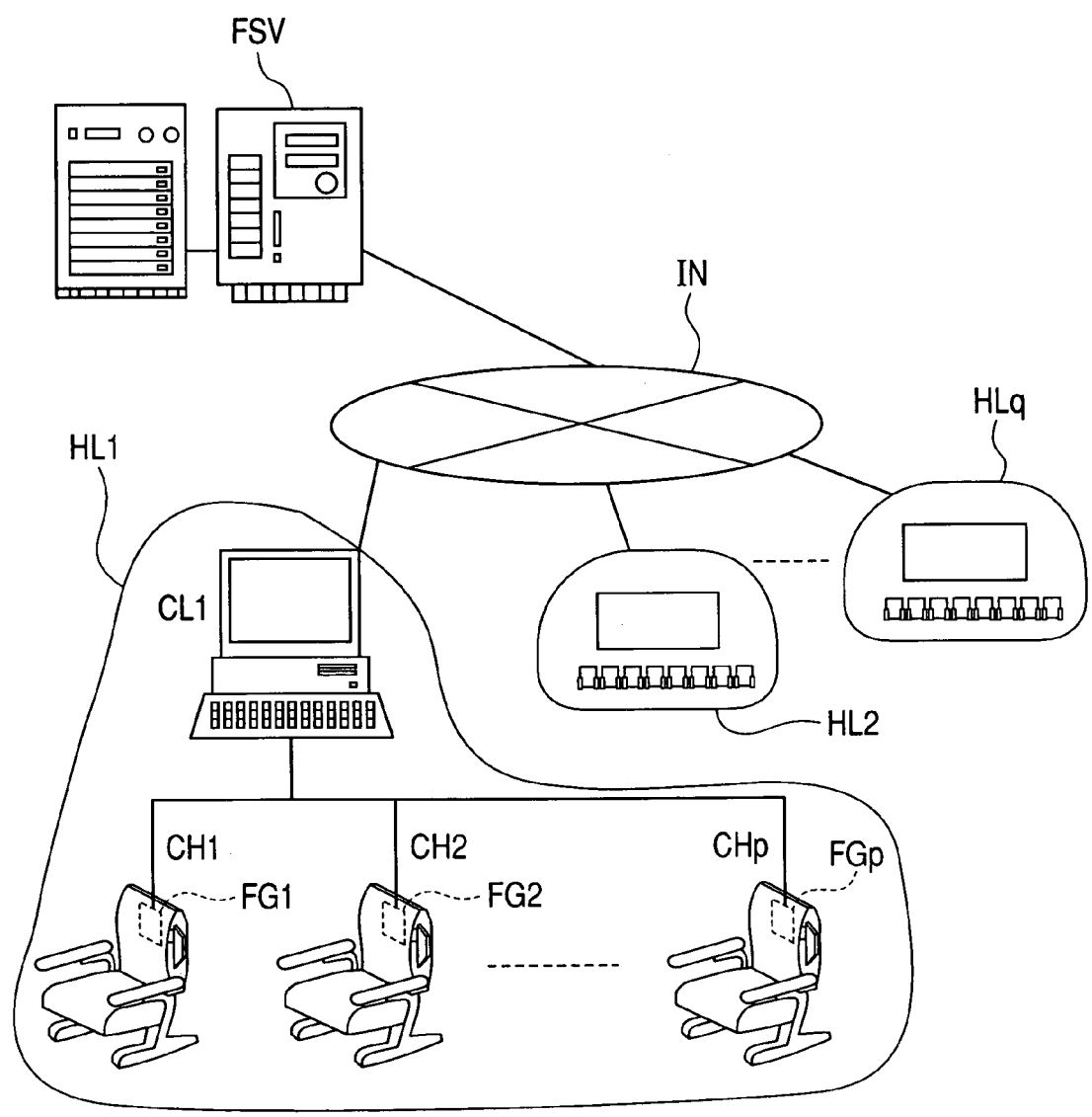
FIG. 25 is a block diagram showing an example where the perfume information processing system is applied to a theater system.

FIG. 25 shows an example where the perfume information processing system is applied to a theater system. In the drawing, each portion that is the same as or equivalent to a portion in FIG. 21 is given the same reference symbol and the description thereof will be omitted.

In FIG. 25, the theater system includes multiple theaters HL1 to HLq and a perfume inquiry server FSV connected to a network IN, with each theater being provided with a client (only a client CL1 of the theater HL1 is shown in the drawing).

In the following description, the theater HL1 will be explained as a representative. In the theater HL1, perfume emitting devices FG1 to FGp are respectively provided for seats CH1 to CHp and are connected to the client CL1 through a LAN.

The client CL1 sends perfume information of contents to be shown and information about perfumes held in the perfume emitting device FG1 to the perfume inquiry server FSV and retrieves a perfume conversion table from the perfume inquiry server FSV.

In the theater system, it is possible to emit a perfume corresponding to contents at each of the seats CH1 to CHp, so it becomes possible to enhance a sense of realism and an atmosphere felt by an audience and to provide a comfortable appreciating environment.

Figure 26:
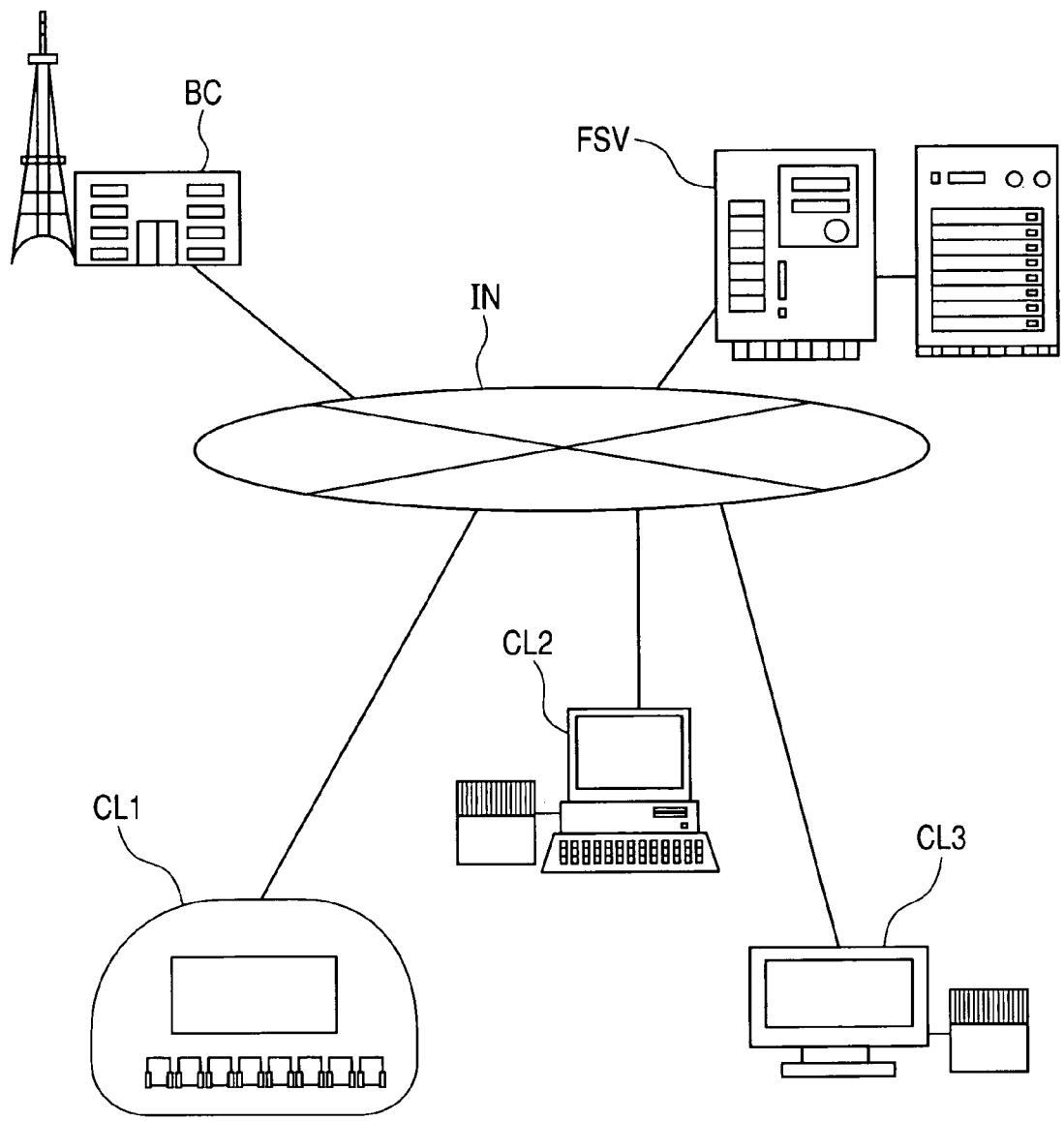
FIG. 26 is a block diagram showing an example where the perfume information processing system is applied to a perfume conversion table providing system.

FIG. 26 shows an example where the perfume information processing system is applied to a perfume conversion table providing system. In the drawing, each portion that is the same as or equivalent to a portion in FIG. 21 is given the same reference symbol and the description thereof will be omitted.

In FIG. 26, the perfume conversion table providing system includes a perfume inquiry server FSV connected to a network IN, with multiple clients CL1 to CL3 and the like also being connected to the network IN. The clients include a perfume information processing device, a theater, a media reproducing system (in which a perfume information processing device is embedded), and a broadcasting station BC.

In response to a perfume conversion table request from a client, the perfume inquiry server FSV generates and sends a perfume conversion table based on perfume information and perfume emitting device information.

Figure 27:
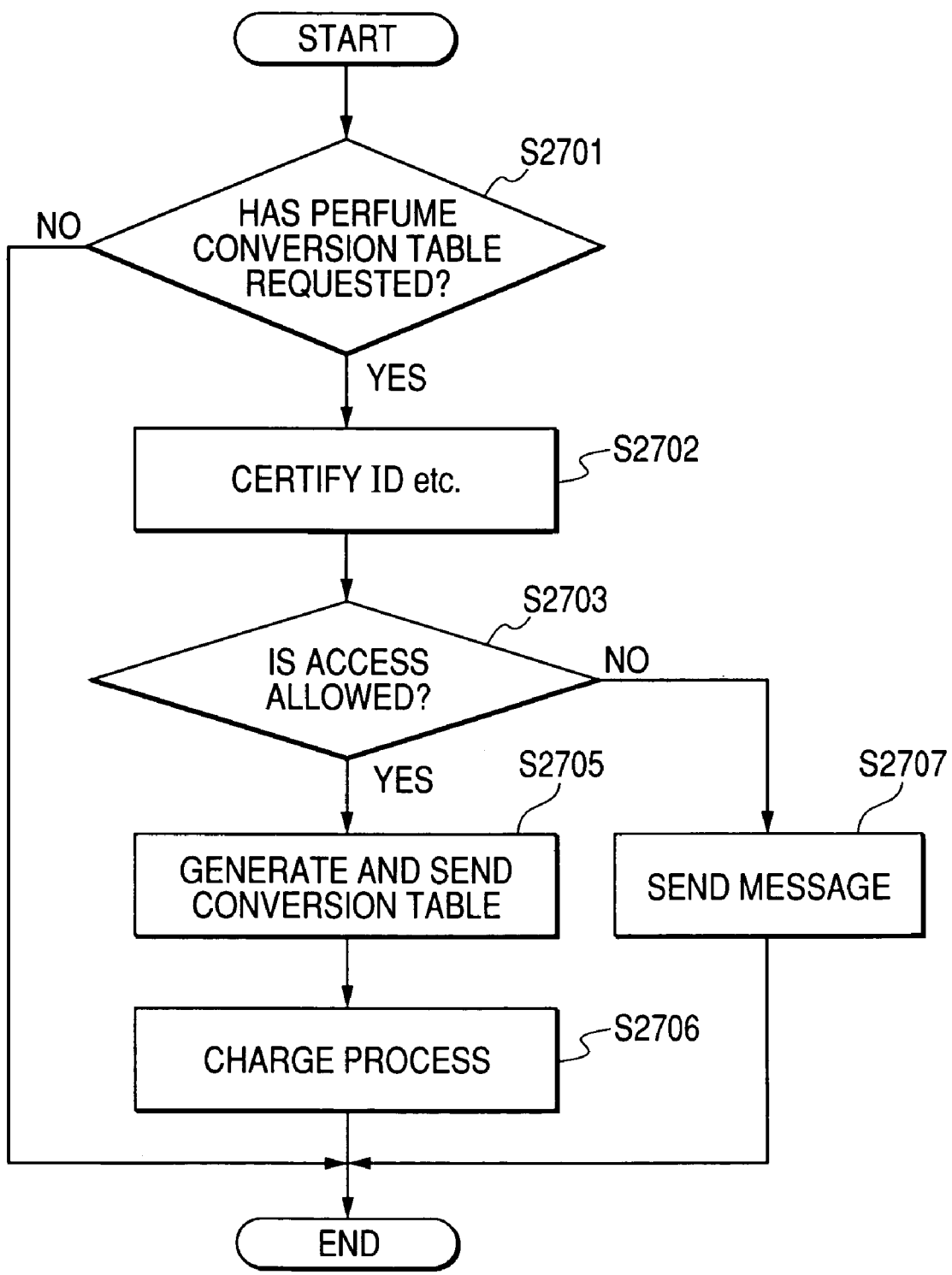
FIG. 27 is a flowchart showing processing of the perfume inquiry server in the perfume conversion table providing system.

FIG. 27 is a flowchart showing a processing procedure of the perfume inquiry server FSV in the perfume conversion table providing system.

In FIG. 27, the perfume inquiry server FSV performs perfume information retrieval, perfume emitting device information retrieval, and a perfume conversion table generation/sending process through respective steps described below.

In step S2701, it is judged whether a perfume conversion table request has been received from the clients CL1 to CL3. Following this, when a result of the judgment is positive, the processing proceeds to step S2702. On the other hand, when the judgment result is negative, the processing is normally ended.

In step S2702, it is judged whether a client having issued the perfume conversion table request has a right to issue the request by means of a user ID, a password, or the like.

In step S2703, it is judged whether the request is allowed based on a result of the judgment in step S2702. When it has been judged that the request is allowed, the processing proceeds to step S2705. On the other hand, when it has been judged that the request is not allowed, the processing proceeds to step S2707.

In step S2705, perfume information and perfume emitting device information are retrieved from the client and a perfume conversion table is generated/sent.

In step S2706, a charge process for the perfume conversion table generation/sending process in step S2704 is performed for the client as necessary. Then, the processing is normally ended.

When the request is not allowed because, for instance, the client does not have an access right, in step S2707, a message to that effect is sent to the client. Then, the processing is normally ended.

The perfume conversion table providing system is capable of providing a perfume conversion table providing service to the client and getting pay for the service.

Second Embodiment

Next, a second embodiment of the perfume information processing device according to the present invention will be described with reference to the drawings.

Figure 32:
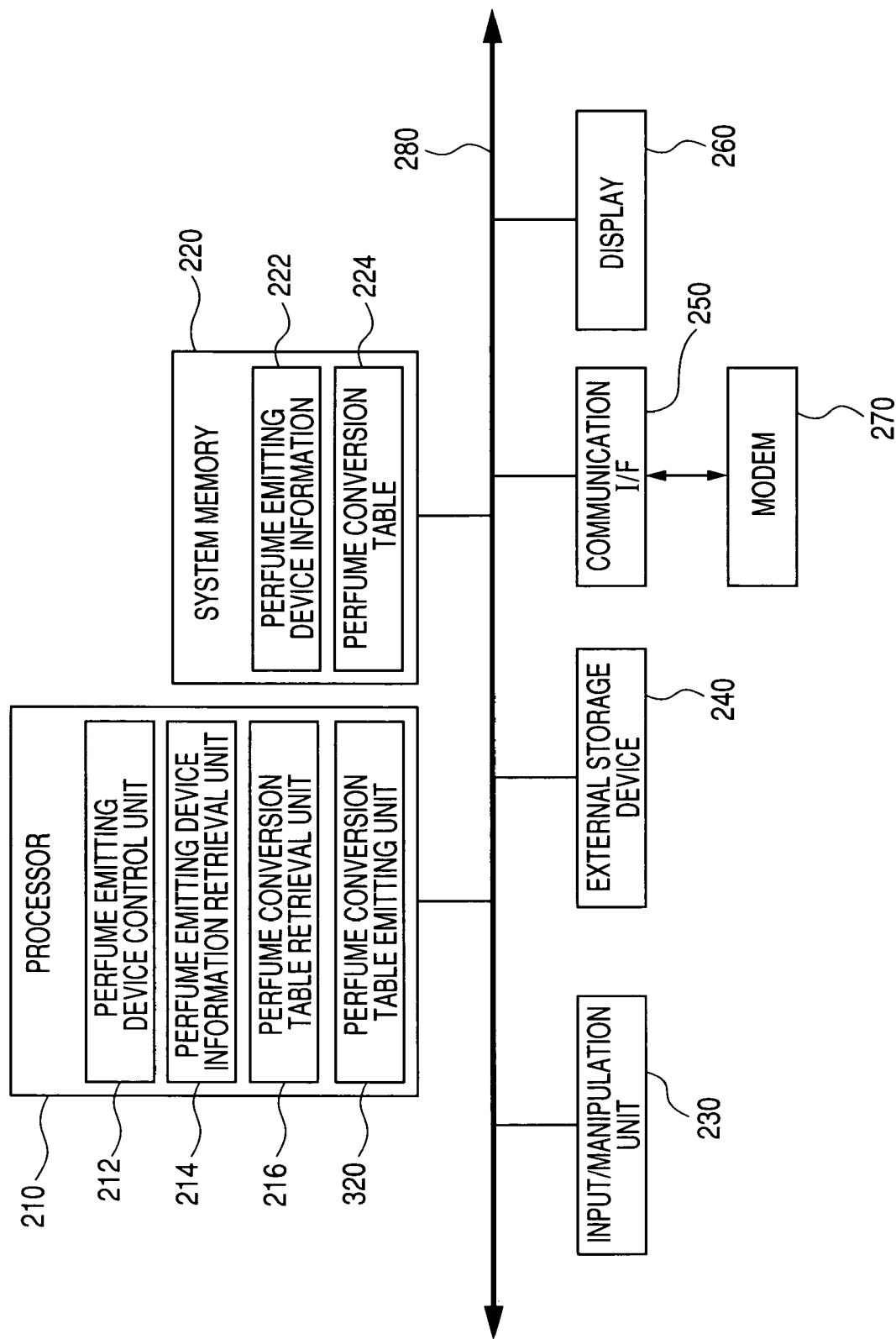
FIG. 32 is a block diagram showing another example of the construction of the perfume information processing device.

FIG. 32 is a block diagram showing the second embodiment of the perfume information processing device. In the drawing, each portion that is the same as or equivalent to a portion in FIG. 2 is given the same reference symbol and the description thereof will be omitted.

In FIG. 32, a perfume emitting device FG1 is connected to a system bus 280 of a perfume information processing device CL1 through an interface 290 and a processor 210, a system memory 220, an input/manipulation unit 230, an external storage device 240, a communication interface 250, and a display 260 are also connected to the system bus 280.

A program 221, perfume emitting device information 222, a perfume conversion table 224, and the like are stored in the system memory 220. Also, a modem 270 is connected to the communication interface 250, with the perfume information processing device CL1 being connected to a network IN through the communication interface 250 and the modem 270.

The processor 210 controls the whole of the perfume information processing device. In addition, the processor 210 functions as a perfume emitting device control unit 212 and a perfume conversion table emitting unit 320.

The perfume conversion table emitting unit 320 generates a perfume conversion table based on the perfume emitting device information 222 and perfume information, which eliminates the necessity to issue a perfume conversion table request to the perfume inquiry server.

That is, the second embodiment of the perfume information processing device is capable of emitting perfume as a standalone device without relying on the perfume inquiry server.

Also, the perfume information processing device itself has a function of the perfume inquiry server, so it is possible to use the perfume information processing device as a perfume inquiry server for another perfume information processing device.

According to the embodiment described above, it becomes possible to increase the number of selectable perfumes.

It should be noted here that the present invention is not limited to the embodiments described above and is applicable not only to a general-purpose computer, such as a personal computer or a large scale computer (main frame), which is usable in various purposes, such as a scientific and technological computation, paperwork, and control, through execution of corresponding software but also to a dedicated computer that dedicatedly solves optimization problems using an optimization algorithm according to the present invention.

Also, the present invention is applicable to any construction so long as it is possible to achieve the functions of the constructions in the embodiments. For instance, it is possible to replace the software construction and the hardware construction in the embodiments described above as appropriate.

In addition, it is also of course possible to attain the objects of the present invention by supplying a system or a device with a storage medium (or a recording medium) recording a program code of software realizing the functions in the embodiments describe above and causing a computer (or a CPU or an MPU) of the system or the device to read and execute the program code stored in the storage medium. In this case, the program code itself read from the storage medium realizes the functions in the embodiments described above and the storage medium storing the program code constitutes the present invention. Also, as a matter of course, the functions in the embodiments described above may be accomplished not only by executing the program code read by the computer but also by causing an operating system (OS) or the like running on the computer to perform a part or all of the actual process based on instructions of the program code.

Further, needless to say, the functions of the above-mentioned embodiments may be accomplished by writing the program code read from the storage medium into a memory provided in a function expansion card inserted into the computer or a function expansion unit connected to the computer and then causing a CPU or the like provided in the function expansion card or the function expansion unit to perform a part or all of the actual processing based on instructions of the program code. When the present invention is applied to the storage medium, a program code corresponding to the flowcharts described above is stored in the storage medium.

Although the present invention has been described in its preferred form with a certain degree of particularity, many apparently widely different embodiments of the invention can be made without departing from the spirit and the scope thereof. It is to be understood that the invention is not limited to the specific embodiments thereof except as defined in the appended claims.

This application claims priority from Japanese Patent Application No. 2004-141736 filed May 12, 2004, which is hereby incorporated by reference herein.

What is claimed is:

1. A perfume information processing device connected to a perfume emitting device that performs perfume emission by emitting a stored perfume, comprising:
   information receiving means for receiving, from the perfume emitting device, stored perfume information representing a plurality of perfumes stored in the perfume emitting device and emission perfume information representing a perfume that should be emitted at the perfume emitting device;
   judgment means for judging whether a perfume corresponding to the emission perfume information representing the perfume that should be emitted is contained among the stored perfumes by referring to correspondences between perfume information and the perfumes;
   first selection means for selecting, when said judgment means judges that the perfume corresponding to the emission perfume information is contained among the stored perfumes, at least one perfume corresponding to the received emission perfume information from among the perfumes represented by the received stored perfume information by referring to correspondences between emission perfume information and perfumes to be emitted;

second selection means for selecting, when said judgment means judges that the perfume corresponding to the emission perfume information is not contained among the stored perfumes, a perfume having a highest point with respect to the emission perfume information from among the stored perfumes by referring to a point of each stored perfume with respect to the emission perfume information;

perfume conversion table generating means for generating a perfume conversion table for converting the emission perfume information into perfume specifying information including information representing the at least one perfume selected by said first and second selection means; and perfume conversion table transmitting means for transmitting the perfume conversion table to the perfume emitting device.

2. A perfume information processing device according to claim 1, wherein the perfume specifying information further includes an emitting parameter of the selected perfume.

3. A perfume information processing device according to claim 2, wherein the emitting parameter includes at least one of an emitting amount, emitting strength, and an emitting time.

4. A perfume information processing device according to claim 1, wherein the emission perfume information contains a sensibility perfume that expresses a perfume using a keyword in a sensibility manner.

5. A perfume information processing device according to claim 4, wherein the sensibility perfume contains an effect perfume suggesting a subject, a background perfume providing an atmosphere, and an emotion perfume corresponding to a feeling.

6. A perfume information processing device according to claim 5, wherein the effect perfume is defined by a layer of a nominal keyword corresponding to the perfume, and the perfume conversion table generating means converts the effect perfume into information showing a perfume, out of the perfumes held in the perfume emitting device, which corresponds to a nominal keyword on a higher layer corresponding to the effect perfume.

7. A perfume information processing device according to claim 5, wherein the background perfume is defined by a point as to an adjectival keyword with respect to the perfume, and the perfume conversion table generating means converts the background perfume into a perfume, out of the perfumes held in the perfume emitting device, whose point as to the adjectival keyword is high.

8. A perfume information processing device according to claim 5, wherein the emotion perfume is defined by a point as to an intransitive keyword with respect to the perfume, and the perfume conversion table generating means converts the emotion perfume into a perfume, out of the perfumes held in the perfume emitting device, whose point as to the intransitive keyword is high.

9. A perfume information processing system comprising:
a perfume emitting device; and
a perfume information processing device according to claim 1.

10. A perfume information processing system according to claim 9, wherein the perfume information processing device includes retrieval means for retrieving information showing a perfume corresponding to contents as information showing a perfume that should be emitted by the perfume emitting device.

11. A perfume information processing system according to claim 10, wherein the contents comprise contents provided from a WEB server.

12. A perfume information processing system according to claim 10, wherein the contents comprise contents provided from a broadcasting medium.

13. A perfume information processing system according to claim 10, wherein the contents comprise contents provided by a recording medium.

14. A perfume conversion table generating method in a perfume information processing device, comprising the steps of:

receiving, from a perfume emitting device, emission perfume information representing a perfume that should be emitted by the perfume emitting device and stored perfume information representing a plurality of perfumes stored in the perfume emitting device;

judging whether a perfume corresponding to the emission perfume information representing the perfume that should be emitted is contained among the stored perfumes by referring to correspondences between perfume information and the perfumes and, when a result of the judgment is positive, selecting the perfume corresponding to the emission perfume information;

selecting, when it is judged that the perfume corresponding to the emission perfume information is not contained among the stored perfumes, a perfume having a highest point with respect to the emission perfume information from among the stored perfumes by referring to a point of each stored perfume with respect to the emission perfume information;

generating a conversion table where the emission perfume information and perfume specifying information including information representing the selected perfume are associated with each other; and transmitting the perfume conversion table to the perfume emitting device.

15. A perfume conversion table generating method according to claim 14, further comprising the steps of:

referring to layer relations with respect to the stored perfume information when the perfume corresponding to the emission perfume information representing the perfume that should be emitted is not contained among the stored perfumes; and selecting a perfume having a highest point with respect to the emission perfume information from among the stored perfumes when at least one perfume that is associated with perfume information on a lower layer than the emission perfume information exists among the stored perfumes.

16. A perfume conversion table generating method according to claim 14, wherein the correspondences are defined for a material perfume stemming from an object and for a sensibility perfume where the point expresses the perfume in a sensibility manner.

17. A computer-readable storage medium on which is stored a computer-readable program to execute the method of claim 14.

* * * * *